US005852190A

United States Patent [19]
Pascal et al.

[11] Patent Number: 5,852,190
[45] Date of Patent: Dec. 22, 1998

[54] DIAZEPINOINDOLES AS PHOSPHODIESTERASE IV INHIBITORS

[75] Inventors: Yves Pascal, Rueil-Malmaison; Indres Moodley, Versailles; Alain Calvet, L'Hay-les-Roses; Jean-Louis Junien, Sevres, all of France

[73] Assignee: Institut de Recherche Jouveinal SA, Fresnes, France

[21] Appl. No.: 391,865

[22] Filed: Feb. 22, 1995

[30] Foreign Application Priority Data

Oct. 14, 1994 [FR] France ................................. 94 12282

[51] Int. Cl.⁶ ............................................... C07D 243/24
[52] U.S. Cl. .......................................................... 540/496
[58] Field of Search ............................ 540/496; 514/220

[56] References Cited

U.S. PATENT DOCUMENTS

| | | | |
|---|---|---|---|
| 4,929,614 | 5/1990 | Calvet et al. | 514/214 |
| 4,981,847 | 1/1991 | Sato et al. | 514/211 |
| 5,082,937 | 1/1992 | Calvet et al. | 540/496 |
| 5,155,101 | 10/1992 | Sato et al. | 514/211 |
| 5,248,679 | 9/1993 | Sato et al. | 514/220 |

OTHER PUBLICATIONS

Calvet et al, Chemical Abstracts, vol. 116, entry 6583 (1991).

*Primary Examiner*—John M. Ford
*Attorney, Agent, or Firm*—Todd M. Crissey

[57] ABSTRACT

The invention relates to diazepinoindoles of formula:

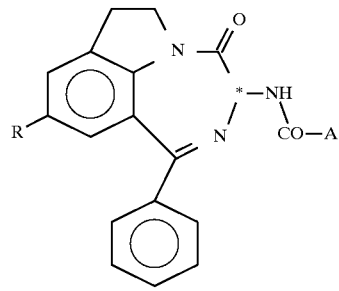

in which R is hydrogen, lower alkyl or lower alkoxy; A is aryl or nitrogen-containing heteroaryl, each of which is optionally substituted by from one to three groups of halogen, lower alkyl, haloalkyl, lower alkoxy and acetamido, or their racemic forms, isomers or pharmaceutically acceptable salts, wherein for the racemic forms of the (S) configuration, A is not phenyl, haloalkyl, or 2-indolyl when R is hydrogen, and for the racemic forms of the (R) configuration, A is not 2-indolyl when R is hydrogen. Also, the invention relates to a method for inhibiting cyclic nucleotide phosphodiesterase activity by administering these compounds to a subject in an amount which is therapeutically effective to inhibit cyclic nucleotide phosphodiesterase activity.

5 Claims, No Drawings

DIAZEPINOINDOLES AS PHOSPHODIESTERASE IV INHIBITORS

FIELD OF THE INVENTION

The present invention relates to the use of [1,4]diazepino[6,7,1-hi] indoles, some of which are novel, for the preparation of medicaments enabling the treatment of disorders for which therapy by a phosphodiesterase IV inhibitor is relevant. These medicaments are useful in particular as antiinflammatory agents, antiallergic agents, bronchodilators or antasthmatics, and are devoid of secondary effects on the digestive system or heart.

TECHNICAL BACKGROUND OF THE INVENTION

In contrast to the properties disclosed by the present invention, the prior art proposes [1,4]diazepino-[6,7,1-hi] indoles for which antagonist properties with respect to cholecystokinin (CCK) and/or gastrin are described, and which are proposed for disorders of the digestive tract: stomach, intestine, pancreas and gall bladder, and in particular for satiety disorders. Thus European Patent Application No. 340 064 describes compounds of formula:

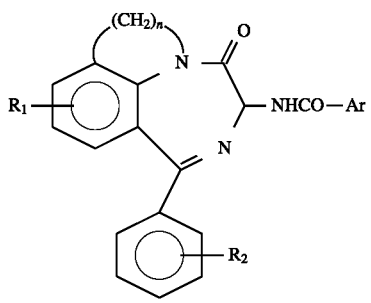

in which $R_1$ and $R_2$ are hydrogen or halogen, Ar is indolyl or phenyl and n is 2 or 3. These compounds are peripheral cholecystokinin antagonists ($CCK_A$).

European Patent Application No. 360 079 describes peripheral and/or central CCK-antagonist compounds of formula:

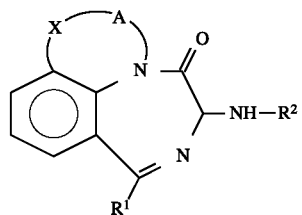

in which $R^1$ is optionally substituted aryl, X is oxygen or methylene which is optionally substituted by a lower alkyl radical, A is a bond or lower alkylene which may carry one or more lower alkyl groups, and $R^2$ is hydrogen or acyl in an excessively wide sense. In fact it appears that the preferred products of this application EP 360 079 are those in which:

$R^1$ [sic] is 2-fluorophenyl and/or $R^2$ [sic] is an aryl-propenoyl or heteroaryl-propenoyl group, and/or the configuration about the diazepine carbon in the α position to its carbonyl function is (S) or (R,S). With regard to the inhibition of phosphodiesterases, it is recalled that cyclic adenosine 3',5'-monophosphate (cAMP) is a universal secondary intracellular messenger, intermediate between a primary messenger (a hormone, neurotransmitter or autocoid) and the cellular functional responses: the primary messenger stimulates the enzyme which is responsible for the synthesis of cAMP and the cAMP acts, depending on the cells in question, in a large number of functions: metabolic, contractile or secretory. The effects of cAMP end when it is broken down by the cyclic nucleotide phosphodiesterases, which are intracellular enzymes which catalyse its hydrolysis to inactive adenosine 5'-monophosphate.

In mammals a distinction is made between at least five major classes of cyclic nucleotide phosphodiesterases (PDEs) numbered from I to V according to their structure, their kinetic characteristics, their substrate specificity or their sensitivity to effectors (Beavo J. A. (1990) Trends Pharmacol. Sci. 11, 150–155). The PDEs IV are specific for cAMP.

Nonspecific phosphodiesterase inhibitor compounds are known which inhibit several classes of enzymes. This is the case for some methylxanthines, such as theophylline. These compounds have a low therapeutic index which results in particular from their action on types of PDE present in cells other than the target cells. In contrast, some classes of PDE can be inhibited selectively by various pharmacological agents: hydrolysis of the cyclic nucleotides is slowed down and thus their concentration increases only in those cells containing the type of PDE which is sensitive to the inhibitor.

Particular interest is evident for phosphodiesterases IV (PDEs IV), which have been identified in numerous tissues including the central nervous system, the heart, the vascular endothelium, the vascular smooth muscle and that of the airways and the myeloid and lymphoid lines.

An increase in cAMP in the cells involved in inflammation inhibits their activation: inhibition of the synthesis and liberation of mediators at the level of the mastocytes, monocytes, eosinophil and basophil polymorphonuclear leucocytes, inhibition of chemotaxis and of the degranulation of neutrophil and eosinophil polymorphonuclear leucocytes, and inhibition of the divisions and differentiation of lymphocytes.

On the other hand, cAMP reduces the tone of the smooth muscular fibres of the airways; PDE IV inhibitors bring about bronchial relaxation.

It is possible therefore to expect that selective PDE IV inhibitors will possess a therapeutic activity as antiinflammatory medicaments, antiallergic medicaments and bronchodilators and in the treatment of asthma, where infiltration of the airways by inflammatory cells and bronchoconstriction are observed.

Theophylline has been very widely used for a long time in the treatment of asthma, and, although its mechanism of action is complex, the inhibition of PDE contributes to its action, but also to certain undesirable effects such as nausea and headaches.

However, the development of powerful PDE IV inhibitors has hitherto proved to be difficult because of the fact that many potential PDE IV inhibitors are not devoid of activity on phosphodiesterases of other classes.

The lack of selectivity of PDE IV inhibitors therefore represents a problem given the extent of the functions regulated by cAMP. There is therefore a need for powerful PDE IV inhibitors which are selective, that is to say do not have an action on PDEs belonging to other classes. Rolipram (INN), a pyrrolidone derivative synthesized first in 1975, is considered to be representative of specific PDE IV inhibitors. Numerous compounds related to rolipram have been synthesized with a view to their use as PDE IV inhibitors. In vitro, rolipram inhibits the activity of inflammatory cells in rodents: inhibition of the synthesis of mediators by the mastocytes, the eosinophil and basophil polymorphonuclear leucocytes, and monocytes; inhibition of chemotaxis and of the degranulation of polymorphonuclear leucocytes. Rolipram has been proposed as an antidepressant; however, its use is accompanied by undesirable effects of the type involving nausea and vomiting.

SUMMARY OF THE INVENTION

Departing now from the prior art, it has now been found that [1,4]diazepino[6,7,1-hi]indole derivatives, some of which are novel, are—surprisingly—powerful PDE IV inhibitors at concentrations at which they have little or no action on the other classes of PDE.

The invention relates essentially to the use of diazepinoindoles, some of which are novel, of formula (I)

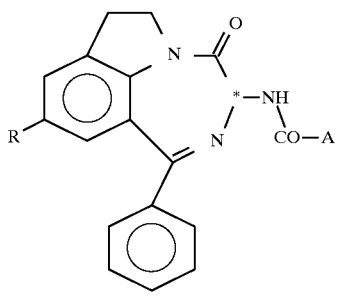

in which:
R is hydrogen, lower alkyl or lower alkoxy, and
A is aryl or nitrogen-containing heteroaryl, each of which is optionally substituted by from one to three groups which are chosen independently from halogen, lower alkyl, haloalkyl, lower alkoxy and acetamido.

DETAILED DESCRIPTION OF THE INVENTION

Firstly, the invention relates to the use, for the preparation of medicaments enabling the treatment of disorders for which therapy by a phosphodiesterase IV inhibitor is relevant, of diazepinoindoles of formula (I)

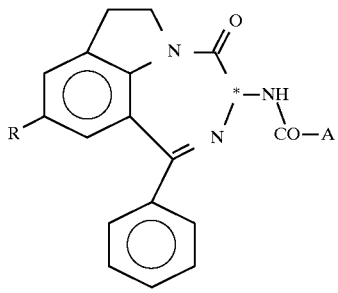

in which:
R is hydrogen, lower alkyl or lower alkoxy; and
A is aryl or nitrogen-containing heteroaryl, each of which is optionally substituted by from one to three groups which are chosen independently from halogen, lower alkyl, haloalkyl, lower alkoxy and acetamido; of their racemic forms, of their isomers whose configuration is determined by the carbon in position 3 of the diazepino-indol-4-one ring system, and of their pharmacologically acceptable salts.

Secondly, the invention relates to the diazepinoindoles of formula (I')

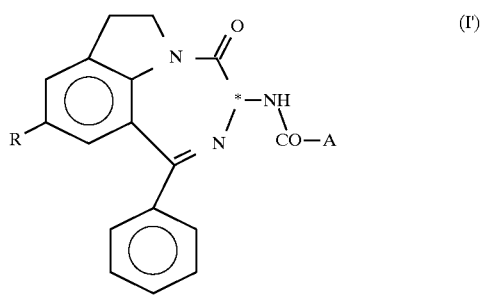

in which:
R is hydrogen, lower alkyl or lower alkoxy; and
A is aryl or nitrogen-containing heteroaryl, each of which is optionally substituted by from one to three groups which are chosen independently from halogen, lower alkyl, haloalkyl, lower alkoxy and acetamido; to their racemic forms and their isomers whose configuration is determined by the carbon in position 3 of the diazepino-indol-4-one ring system, and also to their pharmacologically acceptable salts, with the proviso that:

i) for the racemic forms or those of (S) configuration, when R is hydrogen, A does not, when it is aryl, represent a phenyl radical which is optionally substituted with a halogen or a haloalkyl, and does not, when it is a nitrogen-containing heteroaryl, represent the 2-indolyl radical;

ii) for the forms of (R) configuration, when R is hydrogen, A does not, when it is a nitrogen-containing heterocycle, represent a 2-indolyl radical.

In the text above and that below:
aryl refers to a phenyl or naphthyl group;
nitrogen-containing heteroaryl refers to an unsaturated monocyclic or polycyclic group which contains at least one nitrogen atom, and preferably these nitrogen-containing heterocycles may be four- to seven-membered heteromonocyclic groups containing from 1 to 4 nitrogen atoms, or unsaturated, condensed heterocyclic groups containing from 1 to 4 nitrogen atoms; the nitrogen-containing heteroaryl group may be methylated or ethylated on a positively charged nitrogen;
halogen refers to fluorine, chlorine, bromine or iodine;
lower alkyl refers to linear or branched alkyl groups containing from one to four carbon atoms;
lower alkoxy refers to an 0-alkyl group in which the alkyl group is lower alkyl as defined above; and
haloalkyl refers to a mono-, di- or trihaloalkyl containing from 1 to 4 carbon atoms.

A review of salts which are acceptable in pharmacy can be found in J. Pharm. Sci., 1977, 66, 1–19. However, the phrase pharmacologically acceptable salt of a compound of formula (I) having a basic moiety refers to the addition salts of the compounds of formula (I) which are formed from inorganic or organic, nontoxic acids, for example the salts of hydrobromic, hydrochloric, sulphuric, sulphamic, phosphoric, nitric, acetic, propionic, succinic, glycolic, stearic, lactic, malic, tartaric, citric, mucic, ascorbic, pamoic, maleic, hydroxymaleic, phenylacetic, glutamic, benzoic, salicylic, sulphanilic, acetoxybenzoic, fumaric, toluenesulphonic, ethanedisulphonic, oxalic, isethionic and other acids. The various quaternary ammonium salts of derivatives (I) are likewise included in this category of compounds of the invention. Also, the phrase pharmacologically acceptable salt of a compound of formula (I) having an acidic moiety refers to the usual salts of compounds of formula (I) which are formed from inorganic or organic, nontoxic bases, for example the alkali metal and alkaline earth metal hydroxides (those of lithium, sodium, potassium, magnesium and calcium), amines (dibenzylethylenediamine, trimethylamine, piperidine, pyrrolidine, benzylamine et cetera) or alternatively quaternary ammonium hydroxides such as tetramethylammonium hydroxide.

Among the diazepinoindoles of formula (I) and (I') preference is given to those in which R is lower alkyl or lower alkoxy, and preferably methyl or methoxy. In a general manner, those diazepinoindoles of formula (I) and (I') are preferred in which the asymmetric carbon atom in the alpha position with respect to the carbonyl function of the diazepine ring has the absolute configuration (R) (according to the nomenclature of Cahn, Ingold and Prelog); that is to say the configuration which is opposite to that (S) which is said to be favourable for antagonist-type affinity for CCK receptors.

The invention also relates to a process for the preparation of diazepinoindoles of formula (I) which consists in reacting a racemic or optically active amine of formula (II):

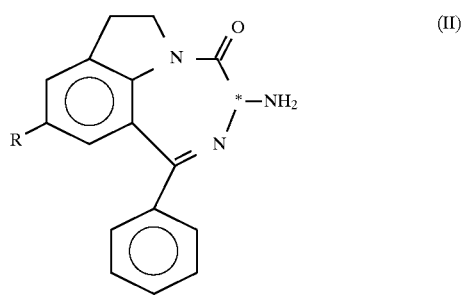

with a carboxylic acid derivative of formula (III):

in which A has the meaning given above and Z is a halogen, an azido group, a 1-imidazolyl group, a group —O—CO—$Z_1$ where $Z_1$ may be, besides A, a hindered alkyl radical containing from 3 to 6 carbon atoms, or else $Z_1$ may be a group O—$Z_2$, with $Z_2$ being an aromatic group containing one or two rings substituted by one or more nitro or halo radicals, to obtain a racemic or optically active compound of formula (I).

Specifically, the preparation of diazepinoindoles of formula (I) will be described in accordance with three methods A, B and C, in which (III) represents the products of formula ($III_A$), ($III_B$) and ($III_C$) respectively:

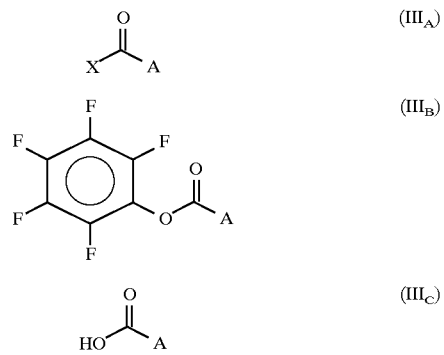

according to the reaction:

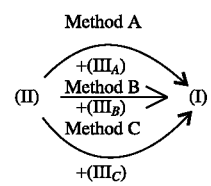

In particular, the following methods are possible:

Method A:

A compound of formula (II) is dissolved in from 5 to 50 volumes of an anhydrous organic solvent such as, for example, a chlorinated hydrocarbon such as dichloromethane or chloroform, a linear or cyclic ether such as 1,2-dimethoxyethane, tetrahydrofuran or dioxane, a polar aprotic solvent such as pyridine, dimethyl sulphoxide or dimethylformamide, or any other solvent which is suitable for bringing about a condensation reaction in this case, or else an appropriate mixture of two or more of these solvents, and from one to two equivalents of an acid halide of formula A—CO—X in which X is halogen, preferably chlorine, and A has the meaning defined above are added thereto.

Subsequently, an equal, equimolar quantity of an organic or inorganic base, preferably triethylamine, is added and the mixture is stirred at a temperature of between −20° C. and the boiling temperature of the mixture for a period of between thirty minutes and 24 hours. The reaction medium, optionally diluted with one of the abovementioned solvents, is then treated in succession with a dilute solution of a mineral acid, then with saturated sodium hydrogen carbonate solution and then with water.

After evaporation of the solvent, the product is generally purified by flash chromatography on a silica column in accordance with a method adapted from Still et al. (1978) J. Org. Chem. 43: 2923.

Method B:

Step 1: A compound of formula A-COOH in which A has the meaning defined above is dissolved in from 5 to 50 volumes of an organic solvent as described for method A. From one to three equivalents of a compound of formula $Z_2$—OH in which $Z_2$ has the meaning indicated above, the groups $Z_2$ preferably being para-nitrophenyl, 2,4-dinitrophenyl and, in particular, pentafluorophenyl, are added in the presence of a dehydrating agent such as a carbodiimide and, optionally, a pyridinium salt. The reaction conditions are similar to those of method A.

After evaporation of the solvent, and depending on its degree of purity as determined by TLC, the product is purified by flash chromatography or employed as in the procedure of step 2.

Step 2: The ester prepared in the preceding step is added to one equivalent of compound (II) dissolved in anhydrous ethyl acetate. The reaction conditions are similar to those of method A. After evaporation of the solvent the product is purified by flash chromatography.

Method C:

A slight excess of the acid of formula A—COOH in which A has the meaning defined above is added directly to a compound of formula (II) in solution in from 5 to 50 volumes of one of the solvents mentioned for method A, in the presence of one equivalent of a condensation agent such as an N,N'-disubstituted carbodiimide, N,N'-carbonyl-diimidazole, or preferably O-[(ethoxycarbonyl)-cyanomethylamino]-N,N,N',N'-tetramethyluronium tetrafluoroborate or else bromo-tris-pyrrolidinophosphonium hexafluorophosphate, and in the presence of two equivalents of a tertiary alkylamine. The operating conditions are similar to those of method A.

The mixture is extracted in succession with a dilute solution of a mineral acid, saturated NaHCO₃ solution and water. After evaporation of the solvent, the product is purified by flash chromatography.

The general process for the preparation of the intermediate amines (II) in their racemic and/or enantiomeric forms is documented in the prior art. For example, it is possible to prepare an amine of formula (II) by aminating, in the alpha position to the carbonyl function, a diazepinoindole of formula (V):

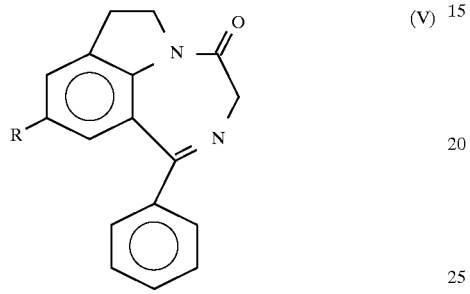

using a hydroxylamine derivative or chloramine; or else, in two steps, by reacting a compound of formula (V) with an oximating reagent, to obtain the oxime of formula (IV):

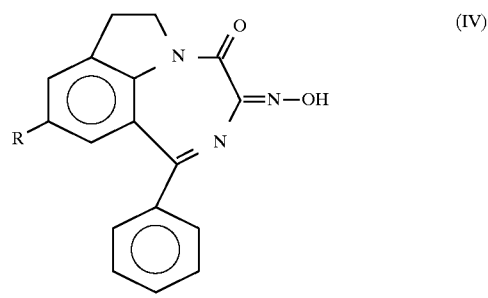

the second step consisting of the catalytic reduction of the oxime by hydrogen in the presence of a reduction catalyst or by reaction with zinc in the presence of acetic acid or with stannous chloride in the presence of hydrochloric acid, to obtain the amine derivative of formula (II). An equation illustrating the process for the synthesis of (II) is given below.

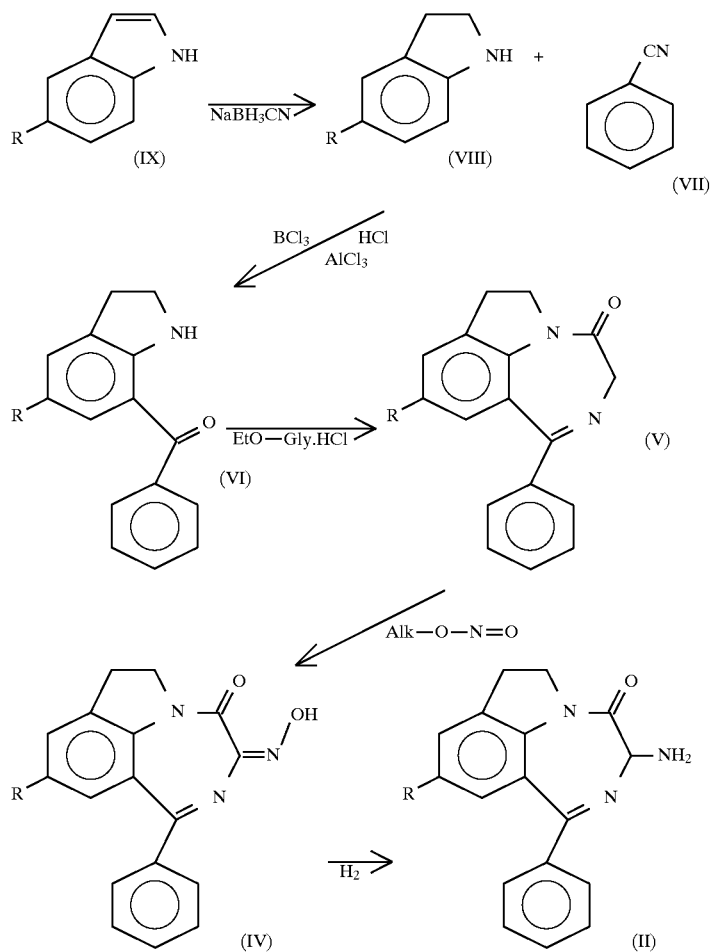

The indole (IX) is reduced to the corresponding indoline (VIII), which is condensed with benzonitrile (VII) in the presence of a Lewis acid to give, after hydrolysis, the benzophenone (VI).

The preparation, from (VI) in the presence of ethyl glycinate in pyridine, of the product of formula (V) is adapted from the method described (method N) by Hester J. B. et al., 1970, J. Med. Chem. 13: 827–835. The possibilities for preparing an optically active compound of formula (II) include:

the condensation of a racemic compound (II) with an alpha-amino acid derivative belonging to the D series or the L series and in which the amine function is protected by a highly labile group, preferably the tert-butyloxy-carbonyl group.

The compound obtained is deprotected by hydrolysis, preferably in acidic medium in the presence of trifluoroacetic acid, and the product obtained is separated into its diastereoisomers by chromatography; the two isomers are obtained of the amine condensed with the amino acid. Edman degradation then yields the two enantiomers with the amine (II); or alternatively the dissolution of a racemic compound (II) in a solution of an optically active acid, for example an enantiomer of mandelic, dibenzoyltartaric, di-p-tolyltartaric, camphorsulphonic, p-nitrobenzoylglutamic or tartaric acid, to form two diastereoisomeric salts followed, utilizing the solubility difference, by selective crystallization of one of them in an appropriate solvent.

The intermediate products of formula (IV) and the products of formula (II) are intermediates which are useful for the preparation of the active products according to the invention.

The invention also relates to a medicament for combating inflammatory and allergic diseases and bronchial constriction, or a medicament which is useful in the treatment of asthma, characterized in that it comprises a diazepinoindole according to the invention in a pharmaceutical form which is suited to the disorder to be treated.

Experimental section
Chemical section

Without limiting the invention, the following examples illustrate the implementation of the processes and the products of the invention. The purity, identity and physicochemical characteristics of the products and of the essential intermediates prepared are determined as follows:

the purity is verified by thin-layer chromatography on silica gel (Merck 60 - F254) and the $R_f$ observed is given for the eluent used, which is most commonly identical to that used for the preparative chromatographic purification of the compounds. These solvents are identified by the following labels:

S.A: methylene chloride,
S.A1: methylene chloride/acetone, 97:3 (v/v),
S.A2: methylene chloride/acetone, 96:4 (v/v),
S.A3: methylene chloride/acetone, 95:5 (v/v),
S.A4: methylene chloride/acetone, 90:10 (v/v),
S.A5: methylene chloride/acetone, 88:12 (v/v),
S.A6: methylene chloride/acetone, 85:15 (v/v),
S.A7: methylene chloride/ethyl acetate, 98:2 (v/v),
S.A8: methylene chloride/methanol, 98:2 (v/v),
S.A9: methylene chloride/methanol, 97:3 (v/v),
S.A10: methylene chloride/methanol, 95:5 (v/v),
S.B: ethyl acetate,
S.B1: ethyl acetate/cyclohexane, 70:30 (v/v),
S.B2: ethyl acetate/cyclohexane, 60:40 (v/v),
S.B3: ethyl acetate/methanol, 97:3 (v/v),
S.B4: ethyl acetate/methanol, 95:5 (v/v), the identity of the empirical formula of the compounds obtained with that of the desired structures is verified by analysis of the principal elements. The results are not given as such but are indicated as being in accordance with the proposed structure, taking into account any solvates or hydrates.

the identity of the products obtained with the proposed structures is verified by their proton nuclear magnetic resonance spectrum and by their infrared spectrography [sic].

The $^1$H NMR spectra are recorded at 400 MHz on a Brücker instrument, the compounds being dissolved in deuterochloroform with tetramethylsilane as internal standard. The nature of the signals, their chemical shifts in ppm, the number of protons they represent and their exchange capacity with $D_2O$ are noted.

The infrared spectra are recorded in the form of a potassium bromide disc on a Shimadzu IR-435 spectrometer.

the physicochemical characteristics given are the melting point, determined by the capillary-tube method and reported as uncorrected values, the optical rotation determined at the ambient temperature of close to 20° C. on a Polartronic apparatus in a 10 cm long tank, the results of which make it possible in some cases to gauge the optical purity by a calculation of the enantiomeric excess (e.e.).

With the aim of standardization, the chemical nomenclature of the products given as examples is that determined with the aid of the "Autonom" software, version 1.0 (Beilstein Institut—Ed. Springler) which generates the systematic nomenclatures of the compounds in accordance with the rules of the IUPAC. Also, for simplification, the nature of the substituent R in the products given as examples is only stated when it is other than H.

Intermediate compounds (II)

Intermediate 1.a: (3RS)-3-Amino-1-phenyl-6,7-dihydro-3H-[1,4]diazepino[6.7,1-hi]indol-4-one (II-R,S).

The compound is prepared according to the procedure described in Example 1 steps a) and b) of EP 0 340 064 A1.

Intermediate 1.b: (3R)-3-Amino-1-phenyl-6,7-dihydro-3H-[1,4]diazepino[6,7,1-hi]indol-4-one (II-R).

The preparation of the compound is described in Example 5 steps a) b) c) g) h) of the experimental section of EP 0 340 064 A1. However, preference is given to an alternative method which consists in the resolution of the racemic intermediate 1.a by the formation and separation of diastereoisomers with N-acetyl-L-phenyl-alanine.

74.0 g (267 mmol) of (3R,S)-3-amino-1-phenyl-6,7-dihydro-3H-[1,4]diazepino[6,7,1-hi]indol-4-one (int. 1.a) are dissolved in 210 ml of boiling n-propanol. Separately, 44.1 g (267 mmol) of N-acetyl-L-phenylalanine are dissolved in 140 ml of boiling n-propanol. The two solutions are mixed, allowed to cool and seeded with a few crystals. After three days at rest the crystals are filtered off and dried. Weight: 50.0 g (e.e.=77%). The product is recrystallized twice in succession from boiling ethyl acetate. 39.0 g are obtained (e.e.=97%). The mother liquors from the first crystallization are evaporated and the residue is taken up in boiling ethyl acetate. After crystallization, filtration and drying 35.0 g of crystals (e.e.=50%) are obtained which, after two successive crystallizations in boiling ethyl acetate, make it possible to obtain 17.0 g (e.e.=97%) of product. When combined the two batches represent 56.0 g (yield=95%) of the salt of the 3R enantiomer of the amine with N-acetyl-L-phenylalanine. m.p. 171° C. $[\alpha]_D=+132°$ (c=1, methanol).

42.4 g (96 mmol) of the salt of the 3R amine are stirred vigorously in the presence of 500 ml of ethyl acetate and 500 ml of normal sodium hydroxide solution. After dissolution the ethyl acetate phase is separated off, washed with saturated aqueous sodium chloride, and then dehydrated and evaporated. 25.4 g of the amine intermediate 1.b. are obtained. Yield=95%. m.p.=79° C. $[\alpha]_{Db\ =172°}$ (c=1, $CH_2Cl_2$).

$^1H$ NMR (ppm): 3.05–3.5 (m, 2H); 3.3 (broad s, 2H exch.); 3.9–4.0 (m, 1H); 4.6–4.7 (m, 1H); 7.05–7.6 (m, 9H). IR: 3350, 1670, 1600, 1560, 1420, 1380, 1340, 1290, 1240, 760, 730, 690 $cm^{-1}$.

Intermediate 2.a: (3R,S)-3-Amino-9-methyl-1-phenyl-6,7-dihydro-3H- [1,4]diazepino[6,7,1-hi]indol-4-one (II - R,S; R=$CH_3$).

Step 1: 5-methylindoline.

28.74 g (457 mmol) of sodium cyanoborohydride are added in small portions at below 20° C. to a solution of 20.0 g (152 mmol) of 5-methylindole in 300 ml of glacial acetic acid. The addition, which is slightly exothermic, is made over 3 hours and is accompanied by slight evolution of hydrogen. The mixture is stirred for 12 hours at below 20° C., and then 300 ml of water are added and the pH of the reaction medium is adjusted to between 10 and 12 by addition of 500 ml of 30% sodium hydroxide solution. The mixture is extracted twice with dichloromethane and the organic phase is washed with 100 ml of water. It is evaporated and the residue is purified by flash chromatography on a silica column, the eluent used being a mixture of increasing polarity of methanol in methylene chloride. 15.3 g (yield=75%) are obtained of a colourless oil which develops a brown colour on storage (under a nitrogen atmosphere with the exclusion of light).

TLC: S.A8; 0.39.

$^1H$ NMR δ(ppm): 2.2 (s, 3H); 2.95 (t, 2H); 3.4 (m, 3H including 1 exch.); 6.5 (d, 1E); 6.8 (d, 1H); 6.95 (s, 1H).

Step 2: 7-benzoyl-5-methylindoline.

13.70 g (103 mmol) of 5-methylindoline are dissolved in 360 ml of 1,2-dichloroethane. 13.24 g (113 mmol) of boron trichloride as a molar solution in dichloromethane are added dropwise at T<5° C., followed by 20.36 g (197 mmol) of benzonitrile and 13.73 g (103 mmol) of anhydrous aluminium trichloride. The mixture is heated at reflux for 16 hours (mass temperature=82°–84° C.). After cooling, hydrolysis is carried out by addition of 103 ml of 4N hydrochloric acid and heating at 80° C. for 20 minutes. The mixture is cooled to about 20° C. and extracted with dichloromethane. The aqueous phase is reextracted with 100 ml of dichloromethane. The combined organic phases are washed with sodium hydroxide solution and then with concentrated sodium chloride solution and dried over sodium sulphate. After filtration and evaporation 22.10 g of a yellow solid are obtained; yield=91%. m.p.=84° C.

Analysis in accordance with $C_{16}H_{15}NO$—TLC: S.A; 0.46

$^1H$ NMR δ(ppm): 2.2 (s, 3H); 3.05 (t, 2H); 3.75 (t, 2H); 6.9 (broad s, 1H exch.); 7.05 (broad s, 2H); 7.5 (m, 3H), 7.65 (m, 2H).

Step 3: 9-methyl-1-phenyl-6,7-dihydro-3H-[1,4]-diazepino[6,7,1-hi]indol-4-one.

21.0 g (88 mmol) of 7-benzoyl-5-methylindoline are introduced into 140 ml of pyridine, followed by 43.2 g (31 mmol) of ethyl glycinate hydrochloride. The mixture is heated at 110°–115° C. with stirring, while distilling the light fractions which are formed. After 12 hours the mixture is cooled, and 150 ml of 2.5% aqueous sodium carbonate solution and 150 ml of dichloromethane are added. The aqueous phase is separated off and extracted with 150 ml of dichloromethane. The organic phases are combined and washed with water. The solvent is evaporated and then the residue is purified by flash chromatography on a silica column, the eluent used being ethyl acetate. 22.0 g of purified product are obtained in the form of a beige-brown solid. Yield=80%. m.p. 132° C.

TLC: S.B; 0.70.

$^1H$ NMR δ(ppm): 2.3 (s, 3H); 3.15 (t, 2H); 4.25 (t, 2H); 4.3 (t, 2H); 7.0 (s, 1H); 7.25 (s, 1H); 7.45 (m, 3H); 7.55 (m, 2H).

Step 4: 3-hydroxyimino-9-methyl-1-phenyl-6,7-dihydro-3H-[1,4]diazepino[6,7,1-hi]indol-4-one.

21.0 g (76 mmol) of the preceding product are dissolved in a mixture of 84 ml of tetrahydrofuran and 168 ml of toluene. The mixture is cooled and 21.3 g (190 mmol) of potassium tert-butylate are added at a temperature below 0° C. The addition is exothermic and the solution takes on a black colour. After stirring for 20 minutes, 9.35 g (80 mmol) of isoamyl nitrite are added over the course of about 10 minutes. Stirring is continued for 10 minutes below 0° C. and then 31.2 ml of glacial acetic acid and 300 ml of water are added. An insoluble component is filtered off, and 200 ml of dichloromethane are added. The phases are separated by settling and the aqueous phase is washed with 200 ml of dichloromethane. The organic phases are combined and washed with 200 ml of water. After evaporation of the solvent, the residue is taken up in 40 ml of methanol. The crystallized product is filtered, washed with 20 ml of cold methanol and then dried. 15.06 g of a yellow solid are obtained. Yield=65%. m.p.=247° C.

TLC: S.B2; 0.38.

$^1H$ NMR δ(ppm): 2.3 (s, 3H); 3.2 (t, 2H); 4.4 (t, 2H); 7.3 (m, 3H); 7.4–7.6 (m, 3H); 7.9 (broad s, 1H)

Step 5: (3R,S)-3-Amino-9-methyl-1-phenyl-6,7-dihydro-3-[1,4]diazepino[6,7,1-hi]indol-4-one.

1.32 g of 5% ruthenium on carbon are added to a solution of 4.4 g (14.4 mmol) of the product obtained in the preceding step, in 150 ml of methanol. The mixture is hydrogenated at 80° C. and a pressure of 8 bar for 6 hours, and then it is filtered and the catalyst is rinsed. After evaporation the residue is purified by flash chromatography on a silica column, the eluent used being a mixture of ethyl acetate which is progressively enriched with methanol. 2.87 g of purified amine are obtained in the form of a yellow-beige solid. Yield=68%. m.p.=116° C.

TLC: S.B4; 0.14.

$^1H$ NMR δ(ppm): 2.3 (s, 3H); 2.4 (broad a, 2H exch.); 3.1 (m, 1H); 3.3 (m, 1H); 3.95 (m, 1H); 4.65 (m, 1H); 7–7.6 (m, 8H).

Intermediate 2.b: (3R)-3-Amino-9-methyl-1-phenyl-6,7-dihydro-3H-[1.4]diazepino(6,7,1-hilindol-4-one. (II-R, R=$CH_3$)

19.95 g (68 imol) of the (R,S) amine 2.a are dissolved in 200 ml of acetonitrile at reflux. Separately, 26.45 g (68 mmol) of di-para-tolyltartaric acid are dissolved at reflux in 260 ml of acetonitrile. The hot solutions are mixed and left to stand for 24 hours at the laboratory temperature. The white crystals are filtered off and washed with 100 ml of cold acetonitrile, and then dried. The optical purity is determined by reacting 5 mg of amine with phenyl 3-methylisocyanate and examining the product obtained on a Pirckle-type chromatography column, eluting with a 50:50 (v/v) mixture of isopropanol/cyclohexane. The filtered crystals, which weigh 20.6 g (e.e.=45%), are recrystallized three times in succession from acetonitrile, in order to obtain the purified product (e.e.=98%). 12.0 g of product are obtained. m.p.=233° C. $[\alpha]_D$=+1770 (c=1, methanol).

The preceding salt is suspended in 100 ml of ethyl acetate. Saturated sodium bicarbonate solution is added with vigorous stirring. After a few minutes the aqueous phase is separated off. The organic phase is washed with water, dried and the solvent is evaporated cold under a nitrogen atmosphere. The purified base is obtained. m.p.=68° C.

$[\alpha]_D$+207° (c=1, $CH_2Cl_2$).

Intermediate 3.a: (3R,S)-3-Amino-9-methoxy-1-phenyl-6,7-dihydro-3H-[1,4]diazepino[6,7,1-hi]indol-4-one. (II—R, S;R=$CH_3O$)

The compound is prepared from 5-methoxyindole in steps, according to the procedure described for the preparation of the intermediate 2.a.

Step 1: 5-Methoxyindoline.
Yield=83%—clear yellow liquid which becomes coloured in light.
TLC: S.B2; 0.38.
$^1$H NMR δ(ppm): 3.0 (t, 2H); 3.41 (s, 1H exch.); 3.5 (t, 2H); 3.7 (s, 3H); 6.6 (s, 2H); 6.8 (s, 1H).

Step 2: 7-Benzoyl-5-methoxyindoline.
Yield=38%—orange solid—m.p.=123° C.
TLC: S.A7; 0.81
$^1$H NMR δ(ppm): 3.05 (t, 2H); 3.65 (s, 3H); 3.75 (t, 2H); 6.75 (broad s, 2H including 1H exch.); 6.95 (broad s, 1H); 7.4–7.55 (m, 3H); 7.65 (m, 2H)

Step 3: 9-Methoxy-1-phenyl-6,7-dihydro-3H-[1,4]-diazepino[6,7,1-hi]indol-4-one.
Yield: 82%—brown resin.
TLC: S.A6; 0.73.
$^1$H NMR δ(ppm): 3.1 (t, 2H); 3.7 (s, 3H); 4.3 (t, 2H); 3.9 (s, 2H); 6.6 (s, 1H); 7.0 (s, 1H); 7.3–7.5 (m, 3H); 7.6 (d, 2H).

Step 4: 3-Hydroxyimino-9-methoxy-1-phenyl-6,7-dihydro-3H-[1,4]diazepino[6,7,1-hi]indol-4-one.
Yield=53%—yellow-orange solid—m.p.=205° C.
TLC: S.A5; 0.17.
$^1$H NMR δ(ppm): 3.2 (t, 2H); 3.7 (s, 3H); 4.4 (t, 2H); 6.7 (t, 2H); 7.1 (s, 1H); 7.4–7.6 (m, 3H); 7.8 (d, 2H); 8.6 (s, 1H).

Step 5: (3R,S)-3-Amino-9-metoxy-1-phenyl-6,7-dihydro-3H-[1,4]diazepino[6,7,1-hi]indol-4-one [sic].
Yield=67%—yellow-beige solid—m.p.=84° C.
TLC: S.B3; 0.24.
$^1$H NMR δ(ppm): 3.2 (t, 2H); 3.7 (8, 3H); 4.4 (t, 2H); 5.3 (s, 1H); 6.7 (s, 1H); 7.1 (s, 1H); 7.4–7.8 (m, 5H); 2.1 and 8.5 (broad B, 2H exch.).

Intermediate 3.b: (3R)-3-Amino-9-methoxy-1-phenyl-6,7-dihydro-3H-[1,4]diazepino[6,7,1-hi]indol-4-one. (II - R; R=$CH_3O$)

10.0 g (32.3 mmol) of the (R,S) amine 3.a are dissolved in 100 ml of acetonitrile at reflux. Separately, 12.47 g (32.3 mmol) of di-para-tolyltartaric acid are dissolved at reflux in 100 ml of acetonitrile. The hot solutions are mixed and then left to crystallize by cooling to the laboratory temperature. After standing overnight, the white crystals are filtered off and washed with 100 ml of cold acetonitrile, and then dried. These crystals (e.e.=37%.) are recrystallized twice in succession from acetonitrile to give the purified product (e.e.= 99.5%). This purification is followed by chromatography on a Pirckle-type $C_{18}$ optically active column, eluting with a 50:50 mixture of isopropanol/ n-hexane. 9.9 g of product are obtained. Yield=44%. m.p.=168° C.

The 9.9 g of the preceding salt are suspended in 100 ml of ethyl acetate. Saturated sodium bicarbonate solution is added with vigorous stirring, and after several minutes the aqueous phase is separated off. The organic phase is washed with 50 ml of water, dried, and then the solvent is evaporated cold under a nitrogen atmosphere. 4.1 g of purified base are obtained. Yield=95%.

m.p.=84° C. $[\alpha]_D$=+23° (c=1.1, $CH_2Cl_2$).

Examples of the invention (I)

As described above, the preparation of the compounds (I) of the invention employs the reaction of the 3-amino-1-phenyl-6,7-dihydro-3H-[1,4]diazepino-[6,7,1-hi]indol-4-one intermediate compounds (II) with halides (III.a) according to method A, with esters, especially pentafluorophenyl esters (III.b) according to method B, or with carboxylic acids (III.c) according to method C. The general procedures for these methods are presented below.

Method A: 10.0 mmol of an intermediate amine (II) are dissolved with stirring in 60 ml of anhydrous methylene chloride in a reactor which is protected against moisture. 10.0 mmol of acid halide (III.a) are then added at a temperature in the region of 20° C., followed by dropwise addition of 10.0 mol of triethylamine. The reaction is continued with stirring at the ambient temperature of between 15° and 25° C., and its progress is monitored by thin-layer chromatography. When the reaction is considered to be at an end, 120 ml of methylene chloride are added to the reaction medium, and the mixture is extracted in succession with 60 ml of 1N HCl solution, 60 ml of saturated sodium bicarbonate solution and finally 60 ml of water. After drying, the methylene chloride is evaporated under reduced pressure, and the residue is purified by flash chromatography on a silica collumn, the eluent being a mixture of increasing polarity consisting, for example, of acetone in methylene chloride. The eluted fractions which are found to contain the pure compound are combined and then evaporated under reduced pressure. The purified product which remains is subjected to the structural determinations and purity analyses described above.

Method B:

Step 1: 10.0 mmol of an intermediate acid (III.c) of formula A-COOH and 3.55 g (19.3 mmol) of pentafluorophenol are dissolved in 25 ml of dichloromethane. 0.81 g (2.6 mmol) of para-dimethylaminopyridinium para-toluenesulphonate is then added, in addition to:

either 22.4 mmol of dicyclohexylcarbodiimide in method "B.a", or 22.4 mmol of N-(3-dimethylaminopropyl)-N'-ethyl-carbodiimide in method "B.b".

The mixture is stirred for 16 hours at the laboratory temperature, which is in the region of 20° C., and then the insoluble components are filtered off. The solvent is removed by distillation and the residue is purified by the technique of flash chromatography on a silica column, the eluent used being most commonly a gradient of acetone in methylene chloride.

The fractions which are found to be pure by TLC are combined, the solvent is evaporated and, after analysis, the residual intermediate ester (IIl.b), in the form of an amorphous foam, is used as it is in the following step.

Step 2: 10.0 mmol of the pentafluorophenyl ester (III.b) prepared in the preceding step are added to 10.0 mmol of intermediate amine (II) dissolved in anhydrous ethyl acetate. After stirring for 16 hours at the ambient temperature, which is in the region of 20° C., the insoluble components are filtered off, the ethyl acetate is evaporated under vacuum, and then the residue is purified by the technique of flash chromatography on a silica column, the eluent used being most commonly a gradient of methanol in methylene chloride. The fractions which are found to be pure by TLC are combined, the solvent is evaporated and the purified residue is identified and analysed.

Method C: 10.0 mmol of an intermediate amine (II) are dissolved with stirring in 50.0 ml of anhydrous methylene chloride in a reactor protected against moisture. At the laboratory temperature, which is in the region of 20° C., 11.0 nmol of an intermediate acid (III.c) of formula A-COOH are added, followed by 10.0 mmol (3.28 g) of "TOTU" (abbreviation for O-[(ethoxycarbonyl)cyanomethyl-amino]-N,N,N',N'-tetramethyluronium tetrafluoroborate—supplied by Fluka ref. 02580). The mixture is cooled to 0° C., then 20.0 mmol (2.55 g) of N,N-diisopropylethylamine are added, after which the mixture is stirred for 12 hours at ambient temperature and then extracted in succession with 50 ml of 1N HCl solution, 50 ml of saturated sodium bicarbonate solution and finally 50 ml of water.

The solvent is evaporated under vacuum and the residue is purified by the technique of flash chromatography on a silica column, the eluent used being most commonly a gradient of methanol in methylene chloride. The fractions which are found to be pure by TLC are combined, the solvent is evaporated and the purified residue is identified and analysed.

EXAMPLE 1.A (3R, S) -2-Chloro-4-trifluoromethylpyrimidine-5-carboxylic acid (4-oxo-1-phenyl-3,4,6,7-tetrahydro[1,4]diazepino[6,7,1-hilindol-3-yl)amide. [(I); A 5- (2-chloro-4-trifluoromethylpyrimidyl)]

The compound is prepared according to method A from the intermediate 1.a and 5-(2-chloro-4-trifluoromethyl) pyrimidylcarboxylic chloride.

Yield=72%—white solid—m.p. 282° C. (decomp.).

Analysis in accordance with $C_{23}H_{15}ClF_3N_5O_2$—TLC: S.A4; 0.70.

$^1$H NMR (DMSO) $\delta$(ppm): 2.9–3.6 (m, 2H); 3.7–4.2 (m, 1H); 4.4–4.75 (m, 1H); 5.45 (d, 1H, becomes s by exch.); 7.1–7.8 (m, 8H); 9.25 (s, 1H); 10.2 (d, 1H exch.) IR: 3200, 1670, 1560, 1540, 1520, 1430, 1345, 1210, 1140, 800, 735, 700 $cm^{-1}$

EXAMPLE 1.B (3R,S)-Imidazo[1,2-a]pyridine-2-carboxylic acid N-(4-oxo-1-phenyl-3,4,6,7-tetrahydro1,4]diazepino-[6,7,1-hi]indol-3-yl)amide. [(I); A=2-imidazo[1,2-a]pyridyl]

The compound is prepared from the intermediate 1.a and imidazo[1,2-a]pyridine-2-carboxylic acid according to a method derived from method C, which consists in carrying out the condensation in tetrahydrofuran (THF) in the presence of bromo-tris-pyrrolidino-phosphonium hexafluorophosphate ("PyBrop") and triethylamine. 4.50 g (16.23 mmol) of the intermediate amine 1.a are dissolved in 150 ml of anhydrous THF. 3.20 g (16.3 mmol) of imidazo[1,2-a]pyridine-2-carboxylic acid and 4.95 g (6.82 ml, 49 mmol) of triethylamine are added. The mixture is cooled by an ice bath, and 9.13 g (18.6 mmol) of "PyBrop" in 50 ml of THF are added. After stirring for 16 hours at the laboratory temperature, the insoluble components are filtered off and the solvents are removed by distillation under vacuum. The residue (12.2 g) is purified by chromatography on a silica column, eluting with ethyl acetate containing 5% acetone. The fractions which are found by TLC to contain the purified product are combined and the solvent is evaporated. 5.1 g of pure product are obtained in an amorphous form. Yield= 71%—m.p.=260° C.

Analysis in accordance with $C_{25}H_{19}FN_5O_2$—$H_2O$—TLC: S.A6; 0.27

$^1$H NMR $\delta$(ppm): 2.80–3.55 (m, 2H); 3.70–4.10 (m, 1H); 4.30–4.75 (m, 1H); 5.50–5.68 (d, 1H s by exch.); 6.65–7.70 (m, 11H); 8.00–8.15 (m, 2H); 8.85–8.95 (d, 1H exch.) IR: 3100, 1725, 1640, 1520, 1390, 1275, 1020, 820, 800, 750 $cm^{-1}$

EXAMPLE 2.A (3R)-2-Fluoro-N-(4-oxo-1-phenyl-3,4,6,7-tetrahydro[1,4]diazepino[6,7,1-hi] indol-3-yl) -benzamide [(I); A =2-fluorophenyl]

Compound prepared according to method A from the intermediate 1.b and 2-fluorobenzoyl chloride.

Yield=50.5%—amorphous solid—m.p.=192° C.—$[\alpha]_D$+ 51° (c=1, $CH_2Cl_2$)

Analysis in accordance with $C_{24}H_{18}FN_3O_2$—TLC: S.A3; 0.43

$^1$H NMR $\delta$(ppm): 3.10–3.20 (m, 1H); 3.30–3.45 (m, 1H); 3.95–4.05 (m, 1H); 4.65–4.75 (m, 1H); 5.65 (d, 1H); 7.10–7.60 (m, 11H including 1H exch.); 8.15 (m, 1H), 8.50–8.65 (m, 1H)

IR: 3300, 1640, 1490, 1430, 1380, 1340, 1230, 1160, 725, 690 $cm^{-1}$

EXAMPLE 2.B (3R)-3-Fluoro-N-(4-oxo-1-phenyl-3,4,6,7-tetrahydro[1,4]diazepino[6,7,1-hi]indol-3-yl)-benzamide [(I); A =3-fluorophenyl]

Compound prepared according to method A from the intermediate 1.b and 3-fluorobenzoyl chloride.

Yield=78%—amorphous solid—m.p.=244° C.—$[\alpha]_D$=+ 48° (c=1, $CH_2Cl_2$)

Analysis in accordance with $C_{24}H_{18}FN_3O_2.0.5H_2O$—TLC: S.A3; 0.43.

$^1$H NMR $\delta$(ppm): 3.15 (m, 1H); 3.35 (m, 1H); 4.00 (m, 1H); 4.65 (m, 1H); 5.60 (d, 1H); 7.10–7.60 (m, 10H); 7.65–7.80 (m, 2H); 8.00 (d, 1H exch.) IR: 3250, 1670, 1620, 1580, 1520, 1430, 1380, 1340, 1280, 1240, 1220, 1140, 790, 670 $cm^{-1}$

EXAMPLE 2.C (3R)-4-Fluoro-N-(4-oxo-1-phenyl-3,4,6,7-tetrahydro[1,4]diazepino[6,7, 1-hi] indol-3-yl) -benzamide [(I); A=4-fluorophenyl]

Compound prepared according to method A from the intermediate 1.b and 4-fluorobenzoyl chloride.

Yield=50.4%—amorphous solid—m.p.=228° C.—$[\alpha]_D$+ 48° (c=1, $CH_2Cl_2$)

Analysis in accordance with $C_{24}H_{18}FN_3O_2.0.25H_2O$—TLC: S.A3; 0.52.

$^1$H NMR $\delta$(ppm): 3.15 (m, 1H); 3.35 (m, 1); 3.95 (m, 1H); 4.65 (m, 1H); 5.60 (d, 1H); 7.10–7.60 (m, 1OH including 1H exch.); 8.00 (m, 1H) IR: 3400, 1640, 1590, 1490, 1440, 1420, 1380, 1340, 1230, 1160, 1050, 800, 760, 690, 660 $cm^{-1}$

EXAMPLE 2.D (3R)-2-Chloro-N-(4-oxo-1-phenyl-3,4,6,7-tetrahydro[1,4]diazepino[6,7,1-hi]indol-3-yl)-benzamide [(I); A=2-chlorophenyll Compound prepared according to method A from the intermediate 1.b and 2-chlorobenzoyl chloride.

Yield=66%—amorphous solid—m.p.=121° C.—$[\alpha]_D$=+ 82° (c=1, $CH_2Cl_2$)

Analysis in accordance with $C_{24}H_{18}FN_3O_2.0.1CH_2Cl_2$—TLC: S.A3; 0.57.

$^1$H NMR $\delta$(ppm): 3.15 (m, 1H); 3.35 (m, 1H); 4.00 (m, 1H); 4.65 (m, 1H); 5.60 (d, 1H); 7.10 (m, 1H); 7.20–7.60 (m, 10H); 7.80 (m, 1H); 8.00 (d, 1H exch.) IR: 3300, 1650, 1590, 1490, 1430, 1380, 1220, 1160, 1040, 750, 730, 690 $cm^{-1}$

EXAMPLE 2.E (3R)-3-Chloro-N-(4-oxo-1-phenyl-3,4,6,7-tetrahydro[1,4]diazepino[6,7,1-hi]indol-3-yl)-benzamide [(I); A =3-chlorophenyl]

Compound prepared according to method A from the intermediate 1.b and 3-chlorobenzoyl chloride.

Yield=85%—white solid—m.p.=-230° C. (decomp.)—[α]$_D$=+34° (c=1, CH$_2$Cl$_2$)

Analysis in accordance with C$_{24}$H$_{18}$ClN$_3$O$_2$—TLC: S.A3; 0.49.

$^1$H NMR δ(ppm): 3.15 (m, 1H); 3.35 (m, 1H); 4.0 (m, 1H); 4.67 (m, 1H); 5.65 (d, 1H, a by exch.); 7.15 (m, 1H); 7.25 (m, 1H); 7.3–7.6 (m, 8H); 7.85 (m, 1H); 8.0 (m, 1E); 8.15 (d, 1H exch.). IR: 3250 (broad), 3050, 1680, 1650, 1505, 1440, 1275, 1240, 725, 690 cm$^{-1}$

EXAMPLE 2.F

3(R)-2-Iodo-N-(4-oxo-1-phenyl-3,4,6,7-tetrahydro[1,4]diazepino[6,7,1-hi]indol-3-yl)-benzamide [(I); A=2-iodophenyl]

Compound prepared according to method A from the intermediate 1.b and 2-iodobenzoyl chloride.

Yield=69%—amorphous solid—m.p.=123° C.—=+81° (c=1, CH$_2$Cl$_2$)

Analysis in accordance with C$_{24}$H$_{18}$IN$_3$O$_2$ TLC: S.A3; 0.55.

$^1$H NMR δ(ppm): 3.15 (m, 1H); 3.40 (m, 1H); 4.0 (m, 1H); 4.67 (m, 1H); 5.65 (d, 1H, s by exch.); 7.12 (m, 2H); 7.25 (m, 1H); 7.3–7.5 (m, 5H); 7.58 (m, 2H); 7.70 (m, 2H, including 1 exch.); 7.92 (d, 1H). IR: 3400, 3260, 1650, 1490, 1440, 1385, 1160, 725, 690 cm$^{-1}$

EXAMPLE 2.G (3R)-3-Chloro-4-fluoro-N-(4-oxo-1-phenyl-3,4,6,7-tetrahydro[1,4]diazepino[6,7,1-hi]indol-3-yl)-benzamide [(I); A=3-chloro-4-fluorophenyl]

Compound prepared according to method C from the intermediate 1.b and 3-chloro-4-fluorobenzoic acid.

Yield=97%—amorphous solid—m.p.=148° C.—[α]$_D$=D+43° (c=1, CH$_2$Cl$_2$)

Analysis in accordance with C$_{24}$H$_{17}$ClFN$_3$O$_2$—TLC: S.A3; 0.70.

$^1$H NMR δ(ppm): 3.15 (m, 1H); 3.35 (m, 1H); 4.00 (m, 1); 4.65 (m, 1H); 5.60 (d, 1H); 7.10–7.60 (m, 9H including 1H exch.); 7.85 (m, 1H); 8.05 (m, 2H) IR: 3300, 3050, 1650, 1480, 1380, 1250, 1170, 1050, 750, 730, 690 cm$^{-1}$

EXAMPLE 2.H (3R)-3,4-Dichloro-N-(4-oxo-1-phenyl-3,4,6,7-tetrahydro[1,4]diazepino[6,7,1-hi]indol-3-yl)-benzamide [(I); A=3,4--dichlorophenyl]

Compound prepared according to method A from the intermediate 1.b and 3,4-dichlorobenzoyl chloride.

Yield=85.4%—amorphous solid—m.p.=163° C.—[α]$_D$=+42° (c=1, CH$_2$Cl$_2$)

Analysis in accordance with C$_{24}$H$_{17}$Cl$_2$N$_3$O$_2$—TLC: S.A3; 0.76.

$^1$H NMR δ(ppm): 3.15 (m, 1H); 3.35 (m, 1H); 4.00 (m, 1H); 4.65 (m, 1H); 5.60 (d, 1H); 7.10–7.60 (m, 9H including 1H exch.); 7.85 (m, 1H); 8.05 (m, 2H) IR: 3300, 3050, 1640, 1500, 1440, 1380, 1280, 1230, 1130, 1020, 750, 730, 690 cm$^{-1}$

EXAMPLE 2.1

(3R)-2-Methyl-N-(4-oxo-1-phenyl-3,4,6,7-tetrahydro[1,4]diazepino[6,7,1-hi]indol-3-yl)-benzamide [(I); A=2-methylphenyl]

Compound prepared according to method A from the intermediate 1.b and 2-methylbenzoyl chloride.

Yield=33%—white solid—m.p.=154° C.—[α]$_D$=+78° (c=1, CH$_2$Cl$_2$)

Analysis in accordance with C$_{25}$H$_{21}$N$_3$O$_3$—TLC: S.A3; 0.34.

$^1$H NMR δ(ppm): 2.6 (s, 3H); 3.15 (m, 1H); 3.38 (m, 1H); 3.48 (m, 1H); 4.68 (m, 1H); 5.66 (d, 1H s by exch.); 7.12 (m, 1H); 7.25 (m, 3H); 7.3–7.5 (m, 5H); 7.56 (m, 2H); 7.68 (m, 2H, 1H exch.). IR: 3300, 3000, 1650, 1470, 1440, 1380, 1250, 1160, 725, 690 cm$^{-1}$

EXAMPLE 2.J (3R)-2-Methoxy-N-(4-oxo-1-phenyl-3,4,6,7-tetrahydro[1,4]diazepino[6,7,1-hi]indol-3-yl)-benzamide [(I); A=2-methoxyphenyl]

Compound prepared according to method A from the intermediate 1.b and 2-methoxybenzoyl chloride.

Yield=b 72%—white solid—m.p.=228° C. [α]$_D$=+34° (C=1, CH$_2$Cl$_2$)

Analysis in accordance with C$_{25}$H$_{21}$N$_3$O$_3$.(0.25H$_2$O).—TLC:S.A3; 0.53.

$^1$H NMR δ(ppm): 3.15 (m, 1H); 3.37 (m, 1H); 4.0 (m, 1H); 4.08 (s, 3H); 4.67 (m, 1H); 5.70 (d, 1H s by exch.); 7.0–7.15 (m, 3H); 7.25 (m, 1H); 7.38 (m, 2H); 7.45 (m, 3H); 7.55 (m, 2H); 8.25 (m, 1H); 9.85 (m, 1H exch.). IR: 3350, 2900, 1670, 1640, 1590, 1500, 1470, 1380, 1280, 1240, 1170, 1010, 750, 730, 690 cm$^{-1}$

EXAMPLE 2.K (3R)-3-Methoxy-N-(4-oxo-1-phenyl-3,4,6,7-tetrahydro[1,4]diazepino[6.7.1-hi]indol-3-yl)-benzamide [(I); A=3-methoxyphenyl]

Compound prepared according to method A from the intermediate 1.b and 3-methoxybenzoyl chloride.

Yield—74%—white solid—m.p.=181° C.—[α]$_D$=+48° (c=1, CH$_2$Cl$_2$)

Analysis in accordance with C$_{25}$H$_{21}$N$_3$O$_3$—TLC:S.A3; 0.51.

$^1$H NMR δ(ppm): 3.15 (m, 1H); 3.35 (m, 1H); 3.85 (s, 3H); 4.0 (m, IH); 4.65 (m, 1H).; 5.65 (d, 1H s by exch.); 7.10 (m, 2H); 7.25 (m, 1H); 7.35–7.6 (m, 9H); 7.97 (m, 1H exch.) IR: 3400, 2900, 1650, 1600, 1480, 1500, 1475, 1440, 1380, 1275, 1240, 1030, 790, 750, 720, 695 cm$^{-1}$

EXAMPLE 2.L (3R)-4-Methoxy-N-(4-oxo-1-phenyl-3,4,6,7-tetrahydro[1,4]diazepinor6,7,1-hi]indol-3-yl)-benzamide [(I); A=4-methoxyphenyl]

Compound prepared according to method A from the intermediate 1.b and 4-methoxybenzoyl chloride.

Yield=67%—white solid—m.p.=221° C. (decomp.)—[α]$_D$=+51° (c=1, CH$_2$Cl$_2$)

Analysis in accordance with C$_{25}$H$_{21}$N$_3$O$_3$—TLC:S.A3; 0.49.

$^1$H NMR δ(ppm): 3.13 (m, 1H); 3.35 (m, 1H); 3.85 (s, 3H); 4.0 (m, 1H); 4.65 (m, 1H); 5.65 (d, 1H s by exch.); 6.95 (d, 2H); 7.10 (t, 1H); 7.25 (t, 1H); 7.38 (m, 2H); 7.45 (m, 2H); 7.55 (m, 2H); 7.95 (m, 3H including 1 exch.) IR: 3350, 1680, 1650, 1600, 1480, 1390, 1250, 1200, 1030, 840, 760, 725, 695 cm$^{-1}$

EXAMPLE 2.M (3R)-3,4,5-Trimethoxy-N-(4-oxo-1-phenyl-3,4,6,7-tetrahydro[1,4]diazepino[6,7,1-hi]indol-3-yl)-benzamide [(I); A=3,4,5-trimethoxyphenyl]

Compound prepared according to method C from the intermediate 1.b and 3,4,5-trimethoxybenzoic acid.

Yield=81.4%—amorphous solid—m.p.=221° C. (decomp.)—[α]$_D$=+54° (c=1, CH$_2$Cl$_2$)

Analysis in accordance with C$_{27}$H$_{25}$N$_3$O$_5$—TLC: S.A4; 0.76.

$^1$H NMR δ(ppm): 3.15 (m, 1H); 3.35 (m, 1H); 3.90 (d, 9H); 4.00 (m, 1H); 4.65 (m, 1H); 5.60 (d, 1H); 7.10 (m, 1H);

7.15–7.30 (m, 3H); 7.30–7.60 (m, 6H); 7.90 (d, 1H) IR: 3300, 2900, 1640, 1520, 1470, 1300, 1230, 1170, 1120, 1000, 750, 730, 690 cm$^{-1}$

EXAMPLE 2.N
(3R) -2-Methoxy-5-chloro-N- (4-oxo-1-phenyl-3,4,6,7-tetrahydro[1,4]diazepino[6,7,1-hi]indol-3-yl)-benzamide [(I); A=2-methoxy-5-chlorophenyl]

Compound prepared according to method C from the intermediate 1.b and 2-methoxy-5-chlorobenzoic acid.

Yield=90.1%—amorphous solid—m.p. 234° C.—[α]$_D$= zero (c=1, CH$_2$Cl$_2$)

Analysis in accordance with C$_{25}$H$_{17}$ClN$_3$O$_5$—TLC: S.A3; 0.64.

$^1$H NMR δ(ppm): 3.15 (m, 1H); 3.35 (m, 1E); 4.00 (m, 1H); 4.10 (s, 3H); 4.70 (m, 1H); 5.6 (d, 1H); 7.00 (d, 1H); 7.10 (t, 1H); 7.20–7.50 (m, 6H); 7.55 (d, 2H); 8.2 (m, 1H); 9.75 (d, 1H exch.) IR: 3350, 1650, 1590, 1470, 1380, 1260, 1240, 1180, 1010, 730, 690, 640 cm$^{-1}$

EXAMPLE 2.O
(3R)-4-Acetamido-N-(4-oxo-1-phenyl-3,4,6,7-tetrahydro[1,4]diazepino[6,7,1-hi]indol-3-yl)-benzamide [(I); A=4-acetamidophenyl]

Compound prepared according to method Ea from the intermediate 1.b and the intermediate pentafluorophenyl ester obtained with 4-acetamidobenzoic acid.

Yield=32%—amorphous product—m.p.=266° C.—[α]$_D$= +43° (c=1, CH$_2$Cl$_2$)

Analysis in accordance with C$_{16}$H$_{22}$N$_4$O$_3$—TLC: S.B; 0.20.

$^1$H NMR δ(ppm): 2.10 (s, 3H); 3.15 (m, 1H); 3.35 (m, 1H); 4.00 (m, 1H); 4.00 (m, 1H); 4.65 (m, 1H); 5.60 (d, 1H); 7.10–7.60 (m, 8H); 7.65 (d, 2H); 7.85 (d, 2H); 7.95 (d, 1H exch.); 8.35 (broad s, 1H exch.) IR: 3300, 1690, 1740, 1600, 1510, 1440, 1390, 1310, 1260, 1180, 1120, 1020, 860, 760, 730, 700 cm$^{-1}$

EXAMPLE 2.P
(3R)-Pyridine-2-carboxylic acid (4-oxo-1-phenyl-3,4,6,7-tetrahydro[1,4]diazepino[6,7,1-hi]indol-3-yl)amide [(I); A=2-pyridyl]

Compound prepared according to method C from the intermediate 1.b and 2-pyridinecarboxylic acid.

Yield=86.0%—amorphous solid—m.p.=208° C.—[α]$_D$= +57° (c=1, CH$_2$Cl$_2$)

Analysis in accordance with C$_{23}$H$_{18}$N$_4$O$_2$.0.2CH$_2$Cl$_2$.0.1H$_2$O—TLC: S.A3; 0.67.

$^1$H NMR δ(ppm): 3.15 (m, 1H); 3.35 (m, 1H); 4.00 (m, 1H); 4.65 (m, 1H); 5.65 (d, 1H); 7.10 (m, 1H); 7.20–7.60 (m, 8H); 7.85 (m, 1H); 8.20 (d, 1H); 8.65 (d, 1H); 9.70 (d, 1H exch.) IR: 3300, 1660, 1490, 1440, 1380, 1240, 1160, 750, 690 cm$^{-1}$

EXAMPLE 2.Q
(3R)-N-(4-oxo-1-phenyl-3,4,6,7-tetrahydro-[1,4]diazepino[6.7,1-hi]indol-3-yl)isonicotinamide [(I); A=4-pyridyl]

Compound prepared according to method B.a from the intermediate 1.b and the intermediate pentafluorophenyl ester obtained with isonicotinic acid.

Yield=83%—amorphous product—m.p. 234° C.—=+23° (c=1, CH$_2$Cl$_2$)

Analysis in accordance with C$_{25}$H$_{20}$ClN$_3$O$_3$—TLC: S.A10; 0.60.

$^1$H NMR δ(ppm): 3.10 (m, 1H); 3.30 (m, 1); 3.90 (m, 1H); 4.60 (m, 1H); 5.60 (d, 1H); 7.05–7.50 (m, 8H including 1H exch.); 7.75 (m, 2H); 8.50 (m, 1H); 8.70 (m, 2H); IR: 3300, 1640, 1470, 1430, 1380, 1270, 1160, 1110, 1040, 750, 720, 690 cm$^{-1}$

EXAMPLE 2.R
(3R)-1H-Indole-2-carboxylic acid (4-oxo-1-phenyl-3,4,6,7-tetrahydro[1,4]diaze-ino[6,7,1-hi]indol-3-yl)amide [(I); A=2-1H-indolyl]

Compound prepared according to method A from the intermediate 1.b and 1H-indole-2-carboxylic chloride.

Yield=81%—white solid—m.p.=196° C.—[α]$_D$=+74° (c=1, CH$_2$Cl$_2$)

Analysis in accordance with C$_{26}$H$_{19}$N$_4$O$_2$.0.5C$_4$H$_8$O$_2$—TLC: S.A3; 0.62.

$^1$H NMR δ(ppm): 2.8–3.6 (m, 2H); 3.7–4.25 (m, 1H); 4.4–4.7 (1H); 5.55–5.65 (d, 1H s by exch.); 6.9–7.7 (m, 13H); 7.9–7.7 (m, 13H); 7.9–8.1 (d, 1H exch.); 10.05 (s, 1H exch.); IR: 3250, 1685, 1630, 1530, 1440, 1385, 1340, 1235, 740, 690cm$^{-1}$

EXAMPLE 2.S
(3R)-Quinoline-3-carboxylic acid (4-oxo-1-phenyl-3,4,6,7-tetrahydro[1,4]diazepino[6,7,1-hi]indol-3-yl)amide [(I); A=3-quinolyl]

Compound prepared according to method A from the intermediate 1.b and 3-quinolinecarboxylic chloride.

Yield=65%—white solid—m.p.=150° C.—[α]$_D$=+152° (c=1, CH$_2$Cl$_2$)

Analysis in accordance with C$_{27}$H$_{20}$N$_4$O$_2$.0.4H$_2$O—TLC: S.A4; 0.22.

$^1$H NMR δ(ppm): 2.70–3.6 (m, 2H); 3.6–4.15 (m, 1E); 4.3–4.8 (1H); 5.5–5.7 (d, 1H s by exch.); 6.8–8.3 (m, 13H); 8.60–8.8 (m, 1H); 9.2–9.4 (m, 1H) IR: 3300, 1680, 1660, 1510, 1445, 1285, 840, 785, 695cm$^{-1}$

EXAMPLE 2.T
(3R)-Quinoline-6-carboxylic acid (4-oxo-1-phenyl-3,4,6,7-tetrahydro[1,4]diaze-ino[6,7,1-hi]indol-3-yl)amide [(I); A=3-quinolyl]

Compound prepared according to method A from the intermediate 1.b and 6-quinolinecarboxylic chloride.

Yield=57%—white solid—m.p.=182° C.—[α]$_D$+59° (c=1, CH$_2$Cl$_2$)

Analysis in accordance with C$_{27}$H$_{20}$N$_4$O$_2$.0.75H$_2$O—TLC: S.A4; 0.40.

$^1$H NMR δ(ppm): 2.80–3.60 (m, 2H); 3.70–4.30 (m, 1H); 4.50–4.90 (m, 1H); 5.75 (d, 1H s by exch.); 6.90–7.70 (m, 10H); 8.00–8.40 (m, 4H including 1H exch.); 8.55 (m, 1H); 9.00 (m, 1H) IR: 3300, 1680, 1650, 1510, 1490, 1440, 1280, 780, 730, 695 cm$^{-1}$

EXAMPLE 2.U
(3R)-3-Methylquinoline-4-carboxylic acid (4-oxo-1-phenyl-3,4,6,7-tetrahydro[1,4]diazepino[6,7,1-hi]indol-3-yl)amide [(I); A=4-(3-methyl)-quinolyl]

Compound prepared according to method B.a from the intermediate 1.b and the intermediate pentafluorophenyl ester obtained with 3-methylquinoline-4-carboxylic acid.

Yield=94%—amorphous product—m.p.=280° C. (decomp.)

Analysis in accordance with C$_{28}$H$_{22}$N$_4$O$_2$.0.1CH$_2$Cl$_2$—TLC: S.A3; 0.58.

$^1$H NMR δ(ppm): 2.70 (s, 3H); 3.20 (m, 1H); 3.45 (m, 1H); 4.00 (m, 1H); 4.70 (m, 1H); 5.80 (d, 1H); 7.10–7.75 (m, 11H); 8.15 (d, 1H); 8.20 (d, 1H exch.); 8.85 (s, 1H) IR: 3300, 1650, 1600, 1520, 1450, 1390, 1340, 1240, 1160, 760, 700 cm$^{-1}$

EXAMPLE 2.V
(3R)-Isocuinoline-3-carboxylic acid (4-oxo-1-phenyl-3,4,6,7-tetrahdro[1,4]diazerino[6,7,1-hi]indol-3-yl)amide [(I); A=3-isoquinolyl]

Compound prepared according to method B.b from the intermediate 1.b and the intermediate pentafluorophenyl ester obtained with 3-methylquinoline-4-carboxylic acid in the presence of N-(3-dimethylaminopropyl)-N'-ethyl-carbodiimide.

Yield=84%—amorphous product—m.p.=250° C.—[α]$_D$=10° (c=1, CH$_2$Cl$_2$).

Analysis in accordance with C$_{27}$H$_2$ON$_4$O$_2$.0.3H$_2$O.0.15CH$_2$Cl$_2$—TLC: S.A1; 0.25.

$^1$H NMR δ(ppm): 3.12 (m, 1H); 3.38 (m, 1E); 3.75 (s, 3H); 4.0 (m, 1H); 4.63 (m, 1H); 5.72 (d, 1H, s by exch.); 7.12 (m, 1H); 7.28 (m, 1H); 7.35 (m, 2H); 7.47 (m, 2H); 7.59 (m, 2H); 7.72 (m, 2H); 8.0 (d, 1H); 8.1 (d, 1H); 8.65 (s, 1H); 9.28 (s, 1H); 9.86 (d, 1H exch.). IR: 3400, 1670, 1600, 1485, 1450, 1260, 900, 970, 785, 755, 730, 700, 670 cm$^{-1}$ Hydrochloride prepared from the base in propanol containing hydrochloric acid. The crystals obtained are rinsed with ether and dried under vacuum.

m.p.=225° C. [α]$_D$=-416° (c=1, CH$_2$Cl$_2$)—TLC: S.A3; 0.35.

EXAMPLE 2.W

Fluorosulphonate of (3R)-N-methylisoauinolinium-3-carboxylic acid (4-oxo-1-phenyl-3.4,6,7-tetrahydro[1,4]diaze-ino[6,7.1-hi]indol-3-yl)-amide [(I); A=N-Methyl-3-isoquinolinium]

1.0 g (2.31 mmol) of the product of Example.2.V are dissolved in 12 ml of dichloromethane, the solution is cooled to 0° C., and 0.184 g (2.31 mmol) of methyl fluorosulphonate is added thereto. After one hour at 0° C. the temperature is allowed to return to ambient, and then the mixture is evaporated under reduced pressure. The residue is purified by flash chromatography on a silica column, the eluent being a mixture of increasing polarity of acetone in methylene chloride. 1.1 g of the compound are obtained in the form of a white solid. m.p.=228° C., Yield=87%—[α]$_D$=-408° (c=1, CH$_2$Cl$_2$)

Analysis in accordance with C$_{28}$H$_{23}$FN$_4$O$_5$S.0.5H$_2$O—TLC:S.A10; 0.10.

$^1$H NMR δ(ppm): 3.35 (m, 1H); 3.45 (m, 1H); 3.52 (s, 3H); 4.5 (m, 1H); 4.78 (m, 1H); 5.75 (d, 1H, S by exch.); 7.0 (m, 1H); 7.25 (m, 1H); 7.45 (m, 1H); 7.65 (m, 2H); 7.7–7.9 (m, 5H); 8.02 (m, 1H); 8.12 (s, 1H); 8.65 (s, 1H); 9.25 (s, 1H); 10.5 (d, 1H exch.) IR: 3450, 3350, 1680, 1600, 1560, 1480, 1430, 1270, 1070, 770, 700, 580 cm$^{-1}$

EXAMPLE 2.X

Imidazo[1,2-a]pyrimidine-2-carboxylic acid (4-oxo-1-phenyl-3,4,6,7-tetrahydro[1.4]diazepino[6,7,1-hi]indol-3-yl)amide [(I); A=imidazo[1,2-a]pyrimidinyl]

Compound prepared according to method B.a from the intermediate 1.b and the intermediate pentafluorophenyl ester obtained with imidazo[1,2-a]pyrimidine-2-carboxylic acid.

Yield=57%—amorphous product—m.p.=270° C. (decomp.)—[α]$_D$=-21° (c=1, CH$_2$Cl$_2$)

Analysis in accordance with C$_{24}$H$_{18}$N$_6$O$_2$.0.5C$_3$H$_6$O.0.2CH$_2$Cl$_2$—TLC: S.A9; 0.13.

$^1$H NMR (DMSO) δ(ppm): 2.90–3.5 (m, 2H); 3.5–4.20 (m, 1H); 4.2–4.7 (m, 1H); 5.40–5.6 (d, 1H s by exch.); 7.0–7.7 (m, 9H); 7.6–7.8 (m, 1H); 8.0 (s, 1H); 8.6–8.75 (m, 1H); 8.75–8.95 (d, 1H exch.). IR: 3400 (broad), 3200, 1685, 1645, 1530, 1440, 1280, 1220, 1155, 730, 700 cm$^{-1}$

Example 2.Y (3R)-4,7-Dimethyl-pyrazolo[5,1-c][1,2,4]triazine-3-carboxylic acid (4-oxo-1-phenyl-3,4,6,7-tetrahydro[1,4]diazepino[6,7,1-hi]indol-3-yl)amide [(I); A=3-(4,7-dimethyl-pyrazolo[5,1-c]-[1,2,4]triazinyl)]

Compound prepared according to method B.a from the intermediate 1.b and the intermediate pentafluorophenyl ester obtained with 4,7-dimethyl-pyrazolo[5,1-c]-[1,2,4]triazine-3-carboxylic acid.

Yield=46%—white powder—m.p.=260° C.—[α]$_D$+21° (c=1, CH$_2$Cl$_2$)

Analysis in accordance with C$_{25}$H$_{21}$N$_7$O$_2$.0.75H$_2$O—TLC: S.A3; 0.20.

$^1$H NMR δ(ppm): 2.65 (s, 3H); 3.15 (m, 1H); 3.30 (s, 3H); 3.40 (m, 1H); 4.00 (m, 1H); 4.70 (m, 1H); 5.70 (d, 1H); 7.10–7.60 (m, 9H); 9.90 (d, 1H exch.). IR: 3350, 1660, 1600, 1560, 1470, 1390, 1370, 1300, 1230, 1170, 800, 730, 690, 640 cm$^{-1}$

EXAMPLE 3

(3R,S)-Ouinoline-3-carboxylic acid (9-methyl-4-oxo-1-phenyl-3,4,6,7-tetrahydro[1,4]diazepino[6,7,1-hi]indol-3-yl)amide [(I); A=3-quinolyl, R=CH$_3$]

The compound is prepared according to method A from the intermediate 2.a: (3R,S)-3-amino-9-methyl-1-phenyl-6,7-dihydro[1,4]diazepino[6,7,1-hi]indol-4-one and 3-quinolinecarboxylic chloride.

Yield=56%—white solid—m.p.=238° C.

Analysis in accordance with C$_{28}$H$_{22}$N$_4$O$_2$.0.2H$_2$O—TLC: S.A4; 0.18.

$^1$NMR δ(ppm): 2.45 (s, 3H); 3.1 (m, 1E); 3.45 (m, 1H); 3.95 (m, 1H); 4.65 (m, 1H); 5.71 (d, 1H, s by exch.); 7.25–7.65 (m, 8H); 7.85 (m, 1H); 7.95 (d, 1H); 8.2 (d, 1H exch.); 8.25 (d, 1H); 8.8 (s, 1H); 9.45 (s, 1H) IR: 3450 (broad), 3200, 3005, 1690, 1660, 1530, 1430, 1375, 1290, 1245, 1160, 920, 780, 695 cm$^{-1}$

EXAMPLE 4

(3R) -Isoquinoline-3-carboxylic acid (9-methyl-4-oxo-1-phenyl-3,4,6,7-tetrahydro[1,4]diazepino[6,7,1-hi]indol-3-yl)amide [(I); A=3-isoquinolyl, R=CH$_3$]

The compound is prepared according to method B.b by a procedure which is identical to Example 2.V with the intermediate 2.b: (3R)-3-amino-9-methyl-1-phenyl-6,7-dihydro-[1,4]diazepino[6,7,1-hi]indol-4-one.

Yield=93%—white solid—m.p.=130° C.=+8° (c=1, CH$_2$Cl$_2$)

Analysis in accordance with C$_{27}$H$_9$N$_4$O$_2$.0.4H$_2$O.0.15CH$_2$Cl$_2$—TLC: S.A4; 0.17.

$^1$H NMR δ(ppm): 2.35 (s, 3H); 3.1 (m, 1E); 3.35 (m, 1H); 4.0 (m, 1H); 4.65 (m, 1H); 5.7 (d, 1H, s by exch.); 7.25–7.5 (m, 5H); 7.6 (m, 2H); 7.75 (m, 2H); 8 (d, 1H); 8.1 (d, 1H); 8.65 (s, 1H); 8.8 (s, 1H); 9.9 (d, 1H exch.) IR: 3380, 1660, 1490, 1350, 1235, 1160, 740, 695 cm$^{-1}$

EXAMPLE 5

(3R,S)-Isoquinoline-3-carboxylic acid (9-methoxy-4-oxo-1-phenyl-3,4,6,7-tetrahydro[1,4]-diazepino(6,7,1-hilindol-3yl)amide [(I); A=3-isoquinolyl, R=CH$_3$O]

The compound is prepared according to method A from the intermediate 3.a: (3R,S)-3-amino-9-methoxy-1-phenyl-6,7-dihydro[1,4]diazepino[6,7,1-hi]indol-4-one and 3-quinolinecarboxylic chloride.

Yield=40%—white solid—m.p.=204° C.

Analysis in accordance with C$_{28}$H$_2$N$_4$O$_3$.0.33H$_2$O0.33CH$_2$Cl$_2$—TLC: S.B1; 0.25.

$^1$H NMR δ(ppm): 3.1 (m, 1H); 3.35 (m, 1H); 3.75 (s, 3H); 4.0 (m, 1H); 4.7 (m, 1H); 5.7 (d, 1H, s by exch.); 6.7 (broad s, 1H); 7.1 (broad s, 1H); 7.25–7.85 (m, 7H); 7.95 (d, 1H); 8.2 (d, 1H); 8.25 (d, 1H exch.); 8.75 (m, 1H); 9.75 (m, 1H). IR: 3300 (broad), 1660, 1520, 1480, 1390, 1290, 1230, 1120, 780, 700 cm$^{-1}$

EXAMPLE 6.A (3R)-3-Chloro-N-(9-methoxy-4-oxo-1-phenyl-3,4,6,7-tetrahydro[1,4]diazepino[6,7,1-hi]indol-3-yl)benzamide [(I); A=3-chlorophenyl, R=CH$_3$O]

The compound is prepared according to method C from the intermediate 3.b: (3R)-3-amino-9-methoxy-1-phenyl-6,7-dihydro[1,4]diazepino[6,7,1-hi]indol-4-one and 3-chlorobenzoic acid.

Yield=75.9%—amorphous solid—m.p.=119° C.—$[\alpha]_D$=+29° (c=1, $CH_2Cl_2$)

Analysis in accordance with $C_{25}H_{20}ClN_3O_3$—TLC: S.A2; 0.59.

$^1$H NMR δ(ppm): 3.10 (m, 1H); 3.35 (m, 1H); 3.70 (s, 3H); 4.00 (m, 1H); 4.65 (m, 1H); 5.60 (d, 1H); 6.70 (s, 1H°; 7.10 (s, 1H); 7.35–7.65 (m, 7H); 7.85 (d, 1H); 8.00 (s, 1H); 8.05 (d, 1H exch.) IR: 3300, 1660, 1570, 1510, 1460, 1370, 1340, 1260, 1230, 1170, 1140, 1040, 760, 740, 700 cm$^{-1}$

EXAMPLE 6.B (3R)-4-Chloro-N-(9-methoxv-4-oxo-1-phenyl-3,4,6,7-tetrahydro[1,4]diazepino[6,7,1-hi]indol-3-yl)benzamide [(I); A=4-chlorophenyl, R=$CH_3O$]

The compound is prepared according to method A from the intermediate 3.b and 4-chlorobenzoyl chloride.

Yield=83%—white solid—m.p.=175° C.—$[\alpha]_D$=+3.26° (c=1, $CH_2Cl_2$)

Analysis in accordance with $C_{25}H_2OClN_3O_3$.0.25$H_2O$—TLC: S.A3; 0.49.

$^1$H NMR δ(ppm)=3.1 (m, 1H); 3.35 (m, 1H); 3.75 (s, 3H); 4.0 (m, 1H); 4.65 (m, 1H); 5.6 (d, 1H s by exch.); 6.7 (s, 1H); 7.1 (s, 1H); 7.35–7.6 (m, 7H); 7.9 (d, 2); 8.0 (d, 1H exch.). IR: 3300, 2900, 1650, 1470, 1365, 1340, 1265, 1230, 1140, 1085, 840, 750, 700 cm$^{-1}$

EXAMPLE 6.C (3R)-N-(9-methoxy-4-oxo-1-phenyl-3,4,6,7-tetrahydro[1,4]diaze-ino[6,7,1-hi]indol-3-yl)isonicotinamide [(I); A=4-pyridyl, R=$CH_3O$]

The compound is prepared according to method B.a from the intermediate 3.b and the intermediate pentafluorophenyl ester obtained with isonicotinic acid.

Yield=55%—amorphous yellow product—m.p.=220°–224° C.—$[\alpha]_D$=+2.4° (c=1, $CH_2Cl_2$)

Analysis in accordance with $C_{24}H_{20}N_4O_3$.0.15$CH_2Cl_2$—TLC: S.A3; 0.42.

$^1$H NMR δ(ppm): 3.15 (m, 1H); 3.35 (m, 1H); 3.75 (s, 3H); 4.00 (m, 1H); 4.65 (m, 1H); 5.60 (d, 1H s by exch.); 6.70 (s, 1H); 7.10 (s, 1H); 7.25–7.60 (m, 5H); 7.80 (d, 2H); 8.10 (d, 1K exch.); 8.80 (d, 2H) IR: 3350, 1685, 1650, 1525, 1570, 1460, 1230, 695 cm$^{-1}$

EXAMPLE 6.D (3R)-Quinoline-3-carboxylic acid (9-methoxy- 4-oxo-1-phenyl-3,4,6,7-tetrahydro[1,4]diazepino[6,7,1-hi]indol-3-yl)amide [(I); A=3-quinolyl, R=$CH_3O$]

The compound is prepared according to method B.b by a procedure which is identical to Example 2.V with the intermediate 3.b and the pentafluorophenyl ester intermediate of 3-quinolinecarboxylic acid.

Yield=77%—white solid—m.p.=112° C.—$[\alpha]_D$=+4.6° (c=1, $CH_2Cl_2$)

Analysis in accordance with $C_{28}H_{22}N_4O_3$.0.66 $H_2O$—TLC: S.B1; 0.30.

$^1$H NMR δ(ppm): 3.1 (m, 1H); 3.35 (m, 1H); 3.75 (S, 3H); 4.0 (m, 1H); 4.7 (m, 1H); 5.7 (d, 1 s by exch.); 6.7 (broad s, 1H); 7.1 (broad s, 1H); 7.25–7.85 (m, 7H); 7.95 (d, 1H); 8.2 (d, 1H); 8.25 (d, 1H exch.); 8.75 (m, 1H); 9.75 (m, 1H). IR: 3300, 1660, 1520, 1480, 1390, 1290, 1230, 1120, 780, 700 cm$^{-1}$

EXAMPLE 6.E (3R) -Quinoline-6-carboxylic acid (9-methoxy-4-oxo-1-phenyl-3,4,6,7-tetrahydro[1,4]diazepino[6,7,1-hi]indol-3-yl)amide. [(I); A=6-quinolyl, R=$CH_3O$]

The compound is prepared according to method B.b by a procedure which is identical to that of Example 2.V with the intermediate 3.b and the pentafluorophenyl ester intermediate of 6-quinoline carboxylic acid.

Yield=80%—white solid—m.p.=206° C. —$[\alpha]_D$=+2.95° (c=1, $CH_2Cl_2$)

Analysis in accordance with $C_{28}H_{22}N_4O_3H_2O$—TLC: S.A10; 0.43.

$^1$H NMR δ(ppm): 3.15 (m, 1H); 3.4 (m, 1H); 3.75 (s, 3H); 4.0 (m, 1H); 4.7 (m, 1H); 5.65 (d, 1H s by exch.); 6.7 (s, 1H); 7.1 (s, 1H); 7.35–7.65 (m, 6H); 8.2–8.35 (m, 4H, 1H exch.); 8.5 (s, 1H); 9 (m, 1H)). IR: 3400 (broad), 1650, 1470, 1370, 1345, 1270, 1230, 1190, 1140, 840, 780, 700 cm$^{-1}$

EXAMPLE 6.F (3R)-Isoquinoline-3-carboxylic acid (9-methoxy-4-oxo-1-phenyl-3,4,6,7-tetrahydro[1,4]diazepino-[6,7,1-hi]indol-3-yl)amide [(I); A=3-isoquinolyl, $R_2$=$CH_3O$]

The compound is prepared according to method B.b by a procedure which is identical to Example 2.V with the intermediate 3.b and the pentafluorophenyl ester intermediate of 3-isoquinoline carboxylic acid.

Yield=87%—white solid—m.p.=211° C.—$[\alpha]_D$=+0.30° (c=1, $CH_2Cl_2$)

Analysis in accordance with $C_{28}H_{22}N_4O_3$.0.1 $H_2O$.0.1 $CH_2Cl_2$—TLC: S.A1; 0.18.

$^1$H NMR δ(ppm): 3.1 (m, 1H); 3.35 (m, 1H); 3.75 (s, 3H); 4.0 (m, 1H); 4.7 (m, 1H); 5.7 (d, 1H s by exch.); 6.7. (broad s); 7.1 (broad s, 1H); 7.2–7.8 (m, 7H); 8.0 (m, 1H); 8.1 (m, 1H); 8.65 (s, 1H); 9.3 (s, 1H); 9.9 (d, 1H exch.). IR: 3360, 1665, 1500, 1490, 1470, 1345, 1265, 1225, 1145, 700 cm$^{-1}$

EXAMPLE 6.G (3R)-4.7-Dimethylpyrazolo[5,1-c[]1,2,4]-triazine-3-carboxylic acid (9-methoxy-4-oxo-1-phenyl-3,4,6,7-tetrahydro[1,4]diazepino[6,7,1-hi]indol-3-yl)-amide [(I); A 4,7-dimethylpyrazolo[5,1-c][1,2,4]triazinyl, R=$CH_3O$]

The compound is prepared according to method C with the intermediate 3.b and 4,7-dimethylpyrazolo [5,1-c][1,2,4]-triazine-3-carboxylic acid.

Yield=60.9%—amorphous solid—m.p.=95° C.—$[\alpha]_D$+19.6° (c=1, $CH_2Cl_2$)

Analysis in accordance with $C_{26}H_{23}N_7O_3$—TLC: S.A9; 0.82.

$^1$H NMR δ(ppm): 2.60 (s, 3H); 3.05 (m, 1H); 3.25 (s, 3H); 3.30 (m, 1H); 3.65 (s, 3H); 3.90 (m, 1H); 4.60 (m, 1H); 5.60 (d, 1H); 6.60 (s, 1H); 7.00 (s, 2H); 7.25–7.45 (m, 3H); 7.55 (m, 2H); 9.80 (d, 1H exch.) IR: 3350, 1670, 1570, 1530, 1490, 1440, 1370, 1350, 1300, 1260, 1230, 1140, 1040, 800, 780, 740, 700 cm$^{-1}$ Biological section Phosphodiesterase—inhibitory activity The capacity of the compounds of formula (I) of the invention to inhibit cyclic nucleotide phosphodiesterases is evaluated by measuring their $IC_{50}$ (concentration of inhibitor required to inhibit enzymatic activity by 50%). In the case of PDEs IV, this value is compared with the $IC_{50}$ of rolipram, a specific inhibitor of PDE IV, by the ratio of the $IC_{50}$ of rolipram to the $IC_{50}$ of the product to be tested, in relation to the same enzyme preparation.

The different classes of phosphodiesterases are obtained in partially purified form on a DEAE-cellulose column from guinea-pig trachea and dog aorta according to a method adapted from that of W. J. Thompson et al., 1979, Advances in Cyclic Nucleotide Research, Vol. 10: 69–92, ed. G. Brooker et al., Raven Press, New York, and of P. J. Silver et al., 1988, Eur. J. Pharmacol. 150: 85–94.

Subsequently, the measurement of the enzymatic activity of the different classes of PDE, and in particular of the PDEs IV, is carried out according to a method which is likewise adapted from that of W. J. Thompson, ibidem.

For the determination of the $IC_{50}$ the enzymatic activity is measured in the presence of the inhibitor in a range of concentrations from 0.1 to 100 µM.

The following table illustrates the PDE IV-inhibitory activity in comparison with that of rolipram for an enzyme preparation obtained from guinea-pig trachea.

TABLE

PDE IV-inhibitory effect compared with rolipram

| Ex. | $\dfrac{IC_{50}\ \text{rolipram}}{IC_{50}\ \text{example}}$ |
|---|---|
| 1B | 3.7 |
| 2B | 1.2 |
| 2C | 1.2 |
| 2M | 1.3 |
| 2N | 2.5 |
| 2O | 1.9 |
| 2P | 1.5 |
| 2S | 3.3 |
| 2T | 2.0 |
| 2Y | 1.4 |
| 5 | 1.2 |
| 6A | 2.7 |
| 6B | 1.6 |
| 6C | 1.6 |
| 6D | 1.9 |
| 6E | 1.9 |
| 6F | 1.2 |
| 6G | 2.2 |

An examination of the results from the preceding table shows that the products of the invention which were tested in the study inhibit the PDE IV activity more effectively than rolipram, and in a number of cases are from two to three times more active than rolipram.

Moreover, studies carried out on PDEs of different classes, purified from guinea-pig trachea or dog aorta, show that the $IC_{50}$ values obtained with the products of the invention in relation to PDEs of class III and of class I and V are much higher than those measured for the PDEs of class IV.

These results are strong evidence of a powerful and selective inhibitory activity of the products of the invention in relation to PDEs IV.

Toxicology

The subacute oral toxicity of Example 2V was studied in the rat. When administered for two weeks as a 1% aqueous suspension in methyl cellulose at a dose of 100 mg/kg/day, the product showed no activity which could be linked with a toxic effect.

Pharmaceutical section

The products of the invention are administered in the form of compositions which are appropriate to the nature and severity of the disorder to be treated. The daily dose for humans is commonly between 2 mg and 1 g of product, which may be taken in one or more individual doses. The compositions are prepared in forms which are compatible with the intended route of administration, for example tablets, coated tablets, capsules, mouthwashes, aerosols, powders for inhalation, suppositories, gels or suspensions. These compositions are prepared by methods which are familiar to the person skilled in the art, and comprise from 0.5 to 60% by weight of active principle (compound of formula I) and 40 to 99.5% by weight of a pharmaceutical vehicle which is appropriate and compatible with the active principle and with the physical form of the intended composition. By way of example, the composition and the method of preparation of tablets containing a compound of the invention are given below.

| | |
|---|---|
| Active substance of formula (I) | 1 to 75 mg |
| Lactose | 124 to 74 mg |
| Microcrystalline cellulose | 36 to 60 mg |
| Polyvinylpyrrolidone | 6 mg |
| Sodium carboxymethylstarch | 8 mg |
| Magnesium stearate | 1 mg |

Mix the active substance, lactose, microcrystalline cellulose and carboxymethylstarch.

Grind and granulate with the aid of an aqueous or alcoholic polyvinylpyrrolidone solution of appropriate concentration.

Dry the granules and adjust their size distribution.

Mix in the magnesium stearate homogeneously.

Carry out tableting procedure to give 200 mg per tablet.

We claim:

1. The compounds:

(3R,S)-2-Chloro-4-trifluoromethylpyrimidine-5-carboxylic acid (4-oxo-1-phenyl-3,4,6,7-tetrahydro[1,4]diazepino[6,7,1-hi]indol-3-yl)amide;

(3R,S)-Imidazo[1,2-a]pyridine-2-carboxylic acid N-(4-oxo-1-phenyl-3,4,6,7-tetrahydro[1,4]diazepino-[6,7,1-hi]indol-3 -yl)amide;

(3R)-2-Fluoro-N-(4-oxo-1-phenyl-3,4,6,7-tetrahydro[1,4]diazepino[6,7,1 -hi]indol-3-yl)-benzamide;

(3R)-3-Fluoro-N-(4-oxo-1-phenyl-3,4,6,7-tetrahydro[1,4]diazepino[6,7,1 -hi]indol-3-yl)-benzamide (3R)-4-Fluoro-N-(4-oxo-1-phenyl-3,4,6,7-tetrahydro[1,4]diazepino[6,7,1-hi]indol-3-yl)-benzamide;

(3R)-2-Chloro-N-(4-oxo-1-phenyl-3,4,6,7-tetrahydro[1,4]diazepino[6,7,1-hi]indol-3-yl)-benzamide;

(3R)-3-Chloro-N-(4-oxo-1-phenyl-3,4,6,7-tetrahydro[1,4]diazepino[6,7,1-hi]indol-3 -yl)-benzamide;

3(R)-2-Iodo-N-(4-oxo-1-phenyl-3,4,6,7-tetrahydro[1,4]diazepino[6,7,1-hi]indol-3 -yl)-benzamide;

(3R)-3-Chloro-4-fluoro-N-(4-oxo-1-phenyl-3,4,6,7-tetrahydro[1,4]diazepino[6,7,1-hi]indol-3-yl)-benzamide; and (3R)-3,4-Dichloro-N-(4-oxo-1-phenyl-3,4,6,7-tetrahydro[1,4]diazepino[6,7,1-hi]indol-3-yl)-benzamide.

2. The compounds:

(3R)-2-Methyl-N-(4-oxo-1-phenyl-3,4,6,7-tetrahydro[1,4]diazepino[6,7,1-hi]indol-3-yl)-benzamide;

(3R)-2-Methoxy-N-(4-oxo-1-phenyl-3,4,6,7-tetrahydro[1,4]diazepino[6,7,1-hi]indol-3-yl)-benzamide;

(3R)-3-Methoxy-N-(4-oxo-1-phenyl-3,4,6,7-tetrahydro[1,4]diazepino[6,7,1-hi]indol-3-yl)-benzamide;

(3R)-4-Methoxy-N-(4-oxo-1-phenyl-3,4,6,7-tetrahydro[1,4]diazepino[6,7,1-hi]indol-3-yl)-benzamide;

(3R)-3,4,5-Trimethoxy-N-(4-oxo-1-phenyl-3,4,6,7-tetrahydro[1,4]diazepino[6,7, 1-hi]indol-3-yl)-benzamide;

(3R)-2-Methoxy-5-chloro-N-(4-oxo-1-phenyl-3,4,6,7-tetrahydro[1 ,4]diazepino[6,7, 1 -hi]indol-3-yl)-benzamide;

(3R)-4-Acetamido-N-(4-oxo-1-phenyl-3,4,6,7-tetrahydro[1,4]diazepino[6,7,1-hi]indol-3-yl)-benzamide;

(3R)-Pyridine-2-carboxylic acid (4-oxo-1-phenyl-3,4,6,7-tetrahydro[1,4]diazepino[6,7,1-hi]indol-3-yl)amide;

(3R)-N-(4-oxo-1-phenyl-3,4,6,7-tetrahydro[1,4]diazepino[6,7,1-hi]indol-3-yl)isonicotinamide; and (3R)-1H-Indole-2-carboxylic acid (4-oxo-1-phenyl-3,4,6,7-tetrahydro[1,4]diazepino[6,7,1-hi]indol-3-yl)amide.

3. The compounds:

(3R)-Quinoline-3-carboxylic acid (4-oxo-1-phenyl-3,4,6,7-tetrahydro[1,4]diazepino[6,7,1-hi]indol-3-yl)amide;

(3R)-Quinoline-6-carboxylic acid (4-oxo-1-phenyl-3,4,6,7-tetrahydro[1,4]diazepino[6,7,1-hi]indol-3-yl)amide;

(3R)-3-Methylquinoline-4-carboxylic acid (4-oxo-1-phenyl-3,4,6,7-tetrahydro[1,4]diazepino [6,7,1-hi]indol-3-yl)amide;

(3R)-Isoquinoline-3-carboxylic acid (4-oxo-1-phenyl-3,4,6,7-tetrahydro[1,4]diazepino[6,7,1-hi]indol-3-yl)amide;

Fluorosulphonate of (3R)-N-methylisoquinolinium-3-carboxylic acid (4-oxo-1-phenyl-3,4,6,7-tetrahydro[1,4]diazepino[6,7, 1-hi]indol-3-yl)-amide;

Imidazo[1,2-a]pyrimidine-2-carboxylic acid (4-oxo-1-phenyl-3,4,6,7-tetrahydro[1,4]diazepino[6,7,1-hi]indol-3-yl)amide;

(3R)-4,7-Dimethyl-pyrazolo[5,1-c][1,2,4]triazine-3-carboxylic acid (4-oxo- 1-phenyl-3,4,6,7-tetrahydro[1,4]diazepino[6,7,1-hi]indol-3-yl)amide; and (3R,S)-Quinoline-3-carboxylic acid (9-methyl-4-oxo-1-phenyl-3,4,6,7-tetrahydro[1,4]diazepino[6,7, 1-hi]indol-3-yl)amide.

4. The compound:

(3R)-Isoquinoline-3-carboxylic acid (9-methyl-4-oxo-1-phenyl-3,4,6,7-tetrahydro[1,4]diazepino[6,7,1-hi]indol-3-yl)amide.

5. The compounds:

(3R, S)-Isoquinoline-3-carboxylic acid (9-methoxy-4-oxo-1-phenyl-3,4,6,7-tetrahydro[1,4]-diazepino[6,7,1-hi]indol-3-yl)amide;

(3R)-3-Chloro-N-(9-methoxy-4-oxo-1-phenyl-3,4,6,7-tetrahydro[1,4]diazepino[6,7,1-hi]indol-3-yl)benzamide;

(3R)-4-Chloro-N-(9-methoxy-4-oxo-1-phenyl-3,4,6,7-tetrahydro[1,4]diazepino[6,7,1-hi]indol-3-yl)benzamide;

(3R)-N-(9-methoxy-4-oxo-1-phenyl-3,4,6,7-tetrahydro[1,4]diazepino[6,7,1-hi]indol-3-yl)isonicotinamide;

(3R)-Quinoline-3-carboxylic acid (9-methoxy-4-oxo-1-phenyl-3,4,6,7-tetrahydro[1,4]diazepino[6,7,1-hi]indol-3-yl)amide;

(3R)-Quinoline-6-carboxylic acid (9-methoxy-4-oxo-1-phenyl-3,4,6,7-tetrahydro[1,4]diazepino[6,7,1-hi]indol-3-yl)amide;

(3R)-Isoquinoline-3-carboxylic acid (9-methoxy-4-oxo-1-phenyl-3,4,6,7-tetrahydro[1,4]diazepino-[6,7,1-hi]indol-3-yl)amide; and (3R)-4,7-Dimethylpyrazolo[5,1-c][1,2,4]-triazine-3-carboxylic acid (9-methoxy-4-oxo-1-phenyl-3,4,6,7-tetrahydro[1,4]diazepino[6,7,1-hi]indol-3-yl)-amide.

* * * * *